US009770504B2

(12) United States Patent
Vitetta

(10) Patent No.: US 9,770,504 B2
(45) Date of Patent: Sep. 26, 2017

(54) GENERATING PEPTOID VACCINES

(71) Applicant: The Board of Regents of the University of Texas System, Austin, TX (US)

(72) Inventor: Ellen S. Vitetta, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/888,297

(22) PCT Filed: May 2, 2014

(86) PCT No.: PCT/US2014/036613
§ 371 (c)(1),
(2) Date: Oct. 30, 2015

(87) PCT Pub. No.: WO2014/179714
PCT Pub. Date: Nov. 6, 2014

(65) Prior Publication Data
US 2016/0067333 A1 Mar. 10, 2016

Related U.S. Application Data

(60) Provisional application No. 61/819,321, filed on May 3, 2013.

(51) Int. Cl.
*A61K 39/385* (2006.01)
*G01N 33/68* (2006.01)
(Continued)

(52) U.S. Cl.
CPC ............ *A61K 39/385* (2013.01); *A61K 39/00* (2013.01); *G01N 33/577* (2013.01);
(Continued)

(58) Field of Classification Search
CPC ..... A61K 39/385; A61K 39/00; G01N 33/577
(Continued)

(56) References Cited

U.S. PATENT DOCUMENTS

| 4,828,981 A | 5/1989 | Maggio |
| 7,235,632 B1 * | 6/2007 | Kirszenbaum ....... C07K 14/705 530/350 |

(Continued)

FOREIGN PATENT DOCUMENTS

| EP | 0 267 690 | 5/1988 |
| WO | WO 99/33969 | 7/1999 |
| WO | WO 2010/138797 | 12/2010 |

OTHER PUBLICATIONS

Grodzki et al. (Himana Press, Methods in Molecular Biology, vol. 588, 2010, Chapter 5).*
(Continued)

*Primary Examiner* — Larry Riggs
*Assistant Examiner* — Karla Dines
(74) *Attorney, Agent, or Firm* — Parker Highlander PLLC

(57) ABSTRACT

The present invention provides for methods of identifying peptoid mimetics that will mimic B cell epitopes when delivered as vaccine compositions. One aspects of the invention is the use of monoclonal antibody that is broadly protective to select the mimetics, thereby identifying an epitope from a pathogen or other disease-causing agent that will be common among most or all variants of that pathogen or agent.

22 Claims, 11 Drawing Sheets

(51) Int. Cl.
  *A61K 39/00* (2006.01)
  *G01N 33/577* (2006.01)
  *C07K 16/16* (2006.01)
(52) U.S. Cl.
  CPC ..... *G01N 33/6818* (2013.01); *G01N 33/6845* (2013.01); *G01N 33/6878* (2013.01); *A61K 2039/572* (2013.01); *A61K 2039/6081* (2013.01); *C07K 16/16* (2013.01); *C07K 2317/34* (2013.01)
(58) Field of Classification Search
  USPC .......................................................... 506/9
  See application file for complete search history.

(56) References Cited

U.S. PATENT DOCUMENTS

| | | | | |
|---|---|---|---|---|
| 2004/0077840 | A1* | 4/2004 | Granoff | C07K 14/22 530/388.4 |
| 2009/0317828 | A1* | 12/2009 | Klinefelter | G01N 33/6854 435/7.2 |
| 2011/0244500 | A1* | 10/2011 | Shapiro | C07K 14/47 435/23 |
| 2012/0122779 | A1 | 5/2012 | Kirshenbaum et al. | |

OTHER PUBLICATIONS

Simon et al. (PNAS USA, 1992, 89:9367).*
Udugamasooriya et al.(JACS, 2008, 130, pp. 5744-5752).*
Astle et al. (INt J Pept Res Ther, 2008, 14, 223-227).*
Briles et al., "Immunication of humans with recombinant pneumococcal surface protein A (rPspA) elicits antibodies that passively protect mice from fatal infection with *Streptococcus pneumonia* bearing heterologous PspA," *The Journal of Infectious Diseases*, 182:1694-16701, 2000.
Case et al., "A novel platform to generate peptoid-based mimetic vaccines," *AAI Abstract Presentation Book*, Hawaii, May 4, 2013.
Case, "A novel platform to generate synthetic vaccine candidates," Doctoral Thesis, The University of Texas Southwestern Medical Center at Dallas, pp. 1-170, 2012.
Chachu et al., "Antibody is critical for the clearance of murine norovirus infection," *Journal of Virology*, 82(13):6610-6617, 2008.
Desmond et al., "The development of a novel anti-peptoid antibody for a peptoid-based vaccine platform (P4506)," *The Journal of Immunology*, 190(1 Supplement):178.7, 2013.
Diaz et al., "Association of a peptoid ligand with the apical loop of pri-miR-21 inhibits cleavage by Drosha," *RNA*, 20:528-539, 2014.
Katpally et al., "Structure of antibody-neutralized murine norovirus and unexpected differences from viruslike particles," *Journal of Virology*, 82(5):2079-2088, 2008.
Lemley et al., "Identification and characterization of a monoclonal antibody that neutralizes ricin toxicity in vitro and in vivo," *Hybridoma*, 13(5):417-421, 1994.
Maddaloni et al., "Immunological characteristics associated with the protective efficacy of antibodies to ricin," *Journal of Immunology*, 172(10):6221-6228, 2004.
Neal et al., "A monoclonal immunoglobulin G antibody directed against an immunodominant linear epitope on the ricin A chain confers systemic and mucosal immunity to ricin," *Infection and Immunity*, 78(1):552-561, 2010.
PCT International Preliminary Report on Patentability issued in International Application No. PCT/US2014/036613, mailed Nov. 12, 2015.
PCT International Search Report issued in International Application No. PCT/US2014/036613, mailed Sep. 24, 2014.
Wobus et al., "Replication of Norovirus in cell culture reveals a tropism for dendritic cells and macrophages," *PLoS Biology*, 2(12):e432, 2004.
Case et al., "The immunogenicity of peptoid-protein conjugates," *J Vaccines Vaccin.*, 7(4):329, 2016.

* cited by examiner

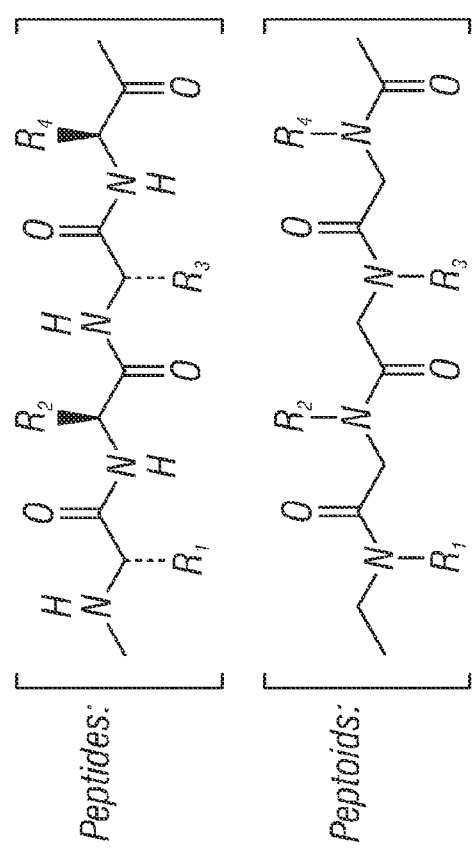
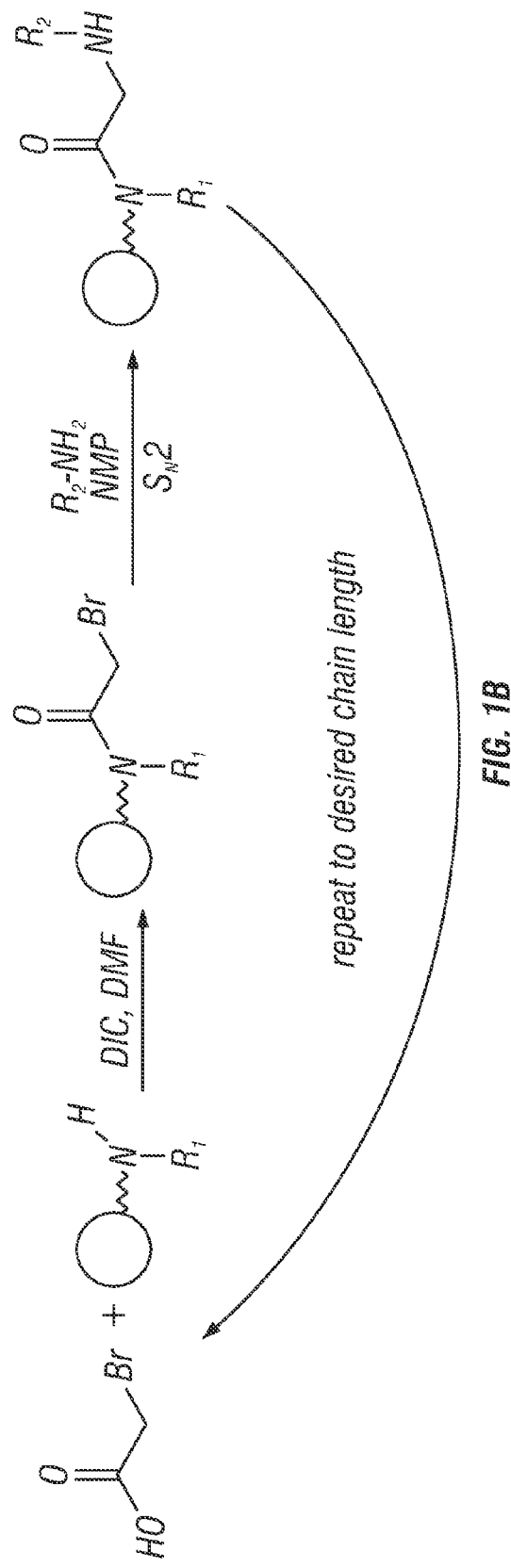
FIG. 1A
FIG. 1B

Tyramine

Glycine

Benzylamine 1,4-Diaminobutane

Isobutylamine (2,2)-Diphenylethylamine

Ethanolamine

Cyclobutylamine

Methoxypropylamine

Tetrahydrofurfurylamine (racemic)

3,4-Dimethoxybenzylamine

1-Boc-4-(aminomethyl)piperidine

Furfurylamine

Piperonylamine 4-(Aminomethyl)pyridine

Histamine

Tryptamine

Allylamine 2-(1-cyclohexenyl)ethylamine

R + Alpha-methylbenzylamine

GENERATING PEPTOID VACCINES

PRIORITY CLAIM

This application is a national phase application under 35 U.S.C. §371 of International Application No. PCT/US2014/036613, filed May 2, 2014, which claims benefit of priority to U.S. Provisional Application Ser. No. 61/819,321, filed May 3, 2013, the entire contents of each of which are hereby incorporated by reference.

GOVERNMENT SUPPORT CLAUSE

This invention was made with government support under Research Grant Number 1RC2CA148271 and fellowship grant number F31A1078740 awarded by the National Institutes of Health. The government has certain rights in the invention.

BACKGROUND OF THE INVENTION

1. Field of the Invention

The present invention relates generally to the field of immunology and in particular, vaccinology. It concerns the identification of immunotherapeutic/immunogenic peptoids and the development of peptoid vaccines for the prevention and treatment of disease.

2. Description of Related Art

According to the Centers for Disease Control, there are over 40 vaccines currently approved for use in the United States. In all cases, these vaccines work by inducing protective immunity, i.e., generating antibodies that can prevent or limit the infection/damage by organisms or toxins that breach epithelial or mucosal barriers, or that can neutralize toxins. In addition to inducing and maintaining long lasting circulating antibody, vaccination schedules are designed to maintain pools of memory lymphocytes that are "on call" for a rapid response to the pathogen or toxin years or even decades later, inducing the production of immunoglobulin (Ig) IgG, IgE, or IgA in the blood or mucosal surfaces, respectively. While these recall responses take a few days to appear, they are often sufficient to abort serious infections. For toxins, which can kill an individual very quickly, antibodies must already be on board in the blood. Cytotoxic T cells are important in resolving intracellular infection, but as far as is known, no approved vaccines work solely by this mechanism; the production of antibody is the major effector mechanism and means of conveying protective and/or sterilizing immunity.

In order to generate a robust IgG, IgE, or IgA response, a molecule must be immunogenic and T cell dependent Immunogenicity is determined by the presence of structural determinants or epitopes on the molecule that can be recognized by two different lineages of lymphocytes, B cells and T cells. Once the B cell epitope on the immunogen is bound to a receptor on a clone of B cells, it is internalized, degraded and peptides from the degraded protein are recycled to the cell surface in human leukocyte antigen (HLA) molecules. These HLA-presented peptides are T cell epitopes. They can be presented on dendritic cells and macrophages as well as B cells. Once the T cells recognize the HLA-peptide on the dendritic cell, and the B cell that initially recognized the native antigen, the helper T cell induces the B cell to differentiate into plasma cells that make antibodies against the B cell epitope (seen by the B cells on the native molecule). Progeny of the helper T cell also help the B cells make IgG, IgE, or IgA of high affinity. If either T cell epitopes or B cell epitopes are lacking on a given molecule, there will rarely be an IgG, IgE or IgA antibody response. However, in the absence of T cell help, some B cell epitopes linked to mitogens or nanoparticles can induce IgM responses.

Several different types of vaccines have been approved for human use. These include live attenuated pathogens, dead pathogens, extracts of pathogens, proteins, subunits, or carbohydrates from pathogens, inactivated toxins, or recombinant proteins. Live attenuated vaccines include polio, mumps, measles, rubella, smallpox, chicken pox and influenza. In general the viruses are grown in non-human cells (such as chicken eggs or simian cells) until they have mutated sufficiently to grow for a limited time in humans but not cause disease. In some cases, mutations are intentionally introduced into the genome of the wild type pathogen to prevent it from causing disease. In other cases, a cross-reactive non-human pathogen is used. In general, these vaccines cause transient infections in a tissue site such as the gut, lung, nasopharynx or skin. Because they grow for a period of time, they induce robust immunity against a variety of B cell epitopes and the antibody responses are long lived. The long lived antibody response is due to long-lived plasma cells and the activation of large pools of memory B and T cells. If given orally or intranasally, live attenuated pathogens can sometimes induce an IgA response in the mucosa which is thought to prevent pathogens from breaching mucosal surfaces in the lung, gastrointestinal and urogenital tracts. The vaccine-induced infection is self-limited by the immune response induced against it. In making these vaccines from live attenuated pathogens, there are several issues that must be considered. First, the pathogen must be sufficiently altered so that it cannot back-mutate and cause disease. Secondly, if individuals are allergic to the cells or components of the cells in which the intracellular pathogens or viruses are grown, they are not eligible to receive the vaccine. Third, (albeit rarely) the vaccines carry the risk of transmitting oncogenic viruses from the non-human cells in which they are grown. Fourth, the immunodominant and protective naturally-expressed epitopes can undergo mutation either within the individual or within the strain of virus from year to year such that frequent vaccinations are necessary and sometimes antibody-resistant organisms emerge. Finally, immunocompromised individuals are at risk for infection because the live organism cannot be cleared or it can survive long enough to revert to the wild-type organism. In general, these vaccines are expensive to make and in some cases there is enough hype about their side effects that individuals refuse to be vaccinated. In certain populations, these infections have therefore reappeared (e.g., Polio and Pertussis).

Dead pathogen vaccines are generally injected intramuscularly with a strong adjuvant to induce the appearance of IgG antibodies in the blood and tissues. It is difficult, but not impossible to induce mucosal immunity with such vaccines, although there are several strategies under study to circumvent this difficulty. If they are given by injection into the muscle or dermis, they can induce a systemic (blood/tissues) antibody response and prevent pathogens or their products from traveling from the site of infection into the bloodstream to another target organ. These vaccines are also expensive to make, and in the case of some, i.e., influenza, the most immunodominant natural epitopes mutate from year to year so that a new vaccine must be manufactured and given annually based on the best prediction of what strain of virus will infect the American public. Sometimes the predictions for the annual strain that will infect the American public are wrong and even if they are correct, annual immunizations are required. In addition, such vaccines can be problematic in the young or elderly where primary immune responses must be made each year and in up to 40% of such individuals, they are not. That is because the young and the elderly often have suboptimal immune systems (except for recall responses in the elderly). It is probably the case that a proportion of individuals in their prime years do not make good antibody responses either, but this is still under study. Compliance is an additional issue. In the case of the human immunodeficiency virus (HIV) or Hepatitis C virus (HCV), dead vaccines would only protect against one or a limited number of subtypes of the virus, since different subtypes have different immunodominant antigens.

Recombinant proteins or subunits vaccines require prior knowledge of the immunoprotective epitopes; they must have both B and T cell epitopes and induce a robust immune response, which is often difficult in the absence of infection or tissue damage. Adjuvants are virtually always necessary to get a robust long-lived response. Obviously, these vaccines must also contain epitopes that are conserved among different strains/clades/or subtypes of the pathogen.

Conjugate vaccines consist of a B cell epitope linked to a carrier protein that contains T cell epitopes. At present, the B cell epitope is generally a carbohydrate to which a young child cannot respond and to which an adult will make only an IgM antibody that does not affinity-mature (i.e., get better with boosting). The selection of the B cell epitope also requires knowledge of the immunogenic carbohydrate or other structure on the pathogen that will elicit neutralizing antibodies. Such vaccines can be effective but they are expensive.

Other vaccines under development include peptides, pathogen genomes packaged in viruses or plasmids, dendritic cell vaccines and anti-idiotypic vaccines. With regard to peptides, these are usually aimed at inducing T cell responses and not antibody responses although there are exceptions. The correct peptides will bind to HLA on antigen presenting cells (APCs) and prime T cells so that they can kill cells infected with intracellular non-lytic pathogens such as HIV or HCV. To design these vaccines the peptide must be of the correct size and have anchoring motifs that bind to the HLA antigens of most of the human species and induce a protective T cell response. Most peptides of this nature are not designed to contain B cell epitopes. It is unknown at this time whether these vaccines will have any utility in humans to induce protective or sterilizing immunity.

In sum, all these vaccines require either inactivated pathogens or extracts thereof or biologically attenuated toxins (called toxoids) or prior knowledge of the immunogen that will induce protective antibody. That immunogen must contain both T and B cell epitopes if production of class-switched IgG or IgA antibody is the goal. All are also expensive to make and several have side effects. Even existing vaccines would benefit from new designs that would make them safer, cheaper, more immunogenic and able to circumvent the problem of genetic drift or mutation of the immunizing epitopes. In addition, there are many pathogens and toxins against which there currently are no effective and/or approved vaccines. These pathogens take a major toll on humans in both developed countries and especially in the third world. Other pathogens and toxins are of concern in this era of bioterrorism. Pathogens not typically endemic in the U.S. can also be a threat to travelers abroad. In our mobile society, emerging infection pathogens such as severe acute respiratory syndrome (SARS) or Ebola virus can be transported around the world in a matter of days. Thus, improved methods of identifying vaccine antigens are urgently needed.

SUMMARY OF THE INVENTION

Thus, in accordance with the present disclosure, there is provided a method of selecting a peptoid mimetic of a protective B cell epitope comprising (a) providing a monoclonal selecting antibody that can inhibit or attenuate a disease, or neutralize a toxin; (b) providing a peptoid library; (c) eliminating from said peptoid library those peptoids that bind outside the antigen combining region of the selecting antibody (antibodies of the same Ig class and from the same species as the said selecting antibody, anti-antibody, protein A/G, or a bead attached thereto), thereby creating a depleted library; (d) adding said selecting antibody to the depleted library of step (c); (e) selecting antibody-bound peptoid from peptoids not bound by said selecting antibody using a ligand for said selecting antibody; and (f) validating the selected peptoids from step (e) by stripping the bound reagents, adding fresh selecting antibody and an enzyme-linked to a ligand that will change color when a substrate for that enzyme is added, wherein a peptoid that binds to said selecting antibody in step (f) is a peptoid mimetic of a protective B cell epitope bound by the selecting antibody. The antigen-combining site of the selecting antibody may bind to a chemical, drug, allergen, toxin, virus, bacterium, fungus, prion, or parasite. The peptoid library may be displayed on a solid support, such as a glass slide, a chip or a population of beads.

Step (e) may comprise (i) using protein A/G-coupled beads to select antibody-bound peptoids; (ii) subjecting protein A/G-bound antibody-peptoid complexes to conditions that release protein A/G from said antibody, and further release said selecting antibody from said peptoid; and (iii) isolating said peptoid from said protein A/G-coupled beads and from said selecting antibody. The protein A/G-decorated beads may be magnetic beads. Alternatively, step (e) may comprises (i) using anti-antibody Ig or an antibody-binding agent such as Protein A or Protein G ligands to select antibody-bound peptoids; (ii) subjecting anti-antibody-bound antibody-peptoid complexes to conditions that release the anti-antibody ligand from said antibody-binding agent, and (iii) further releasing said selecting antibody from said peptoid. The anti-antibody may be linked to a surface or a ligand. The method may further comprise obtaining the sequence of a peptoid selected in step (f). Obtaining information may comprise referencing a code or pattern that correlates to a pre-determined sequence. Alternatively, obtaining may comprise Edman degradation, mass spectrometry, circular dichroism, nuclear magnetic resonance, or X-ray crystallography.

The method may further comprise combining a peptoid selected in step (f) to a carrier molecule that renders the selected peptoid immunogenic, and even further comprise immunizing a vertebrate with said peptoid-carrier complex, such as a non-self protein lacking T and B cell epitopes that cross react with self T and B cell epitopes, e.g., keyhole limpet hemocyanin (KLH), tetanus toxoid or reduced diphtheria toxoid. The carrier molecule may a liposome or nanoparticle. The peptoid may be displayed on said carrier at up to $10^7$ copies per carrier molecule. The method may further comprise assessing the binding of said selecting antibody with said peptoid-carrier complex. The immunizing step may further comprise the addition and co-administration of an adjuvant, such as aluminum salts (phosphate and hydroxide) or other immunostimulatory agent, such as a cytokine, a ligand for a Toll-like receptor (TLR), or liposome or other nanoparticle with said peptoid-carrier complex. Combinations of these agents can also be used. The method may further comprise obtaining post-immunization serum from said vertebrate or passively administering said serum to a non-immunized vertebrate and challenging that vertebrate with the disease-causing entity or toxin. The method may further comprise determining the binding of post-immunization serum to a disease-causing agent or component thereof to which the selecting antibody binds, either directly or in a competitive format with said selecting antibody. The method may further comprise determining the ability of said post-immunization serum to inhibit or attenuate disease, including inhibition or attenuation by complement-dependent neutralization, complement-independent neutralization, direct inhibition of growth, antibody dependent cell mediated cytotoxicity (ADCC), opsonization, inhibition of binding to, or internalization by, a target cell, inhibition of infection or toxicity, elimination by the reticuloendothelial system (RES), or prevention of homing to a site where disease will manifest.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C. Properties of Peptoids. (FIG. 1A) A comparison of the structure of peptides vs. peptoids reveals a common backbone, but a side chain translocation (R1-R4 in the figure) from the alpha carbon atom in peptides to the nitrogen atom in peptoids. This translocation impacts the structure, behavior, and characteristics of peptoids as compared to peptides. (FIG. 1B) Peptoids are synthesized in two steps by the sub-monomer synthesis approach. This figure shows the two step reaction of acylation and displacement. Together, this two-step addition adds a single peptoid monomer to the peptoid chain. (FIG. 1C) Examples of peptoid side groups that can be easily incorporated into the peptoid backbone by sub-monomer synthesis. Almost any aminated side group can be added to the backbone.

(FIG. 2A) In the magnetic screening assay, on-bead peptoids or peptides are incubated with a monoclonal antibody (MAb). On-bead peptoids or peptides bound by the screening MAb are then selected using protein G Dynabeads (PGDs). Protein G (small circle at end of antibody) has a high affinity for the Fc or "tail portion" of antibodies. The iron oxide core of the PGDs (large circle at end of antibody) is magnetic, and upon application of a magnet, the antibody-bound, PGD-bound peptoid or peptide beads can be isolated from on-bead peptoids or peptides that are not bound be the screening antibody. (FIG. 2B) In the color screening assay, on-bead peptoids or peptides isolated in the magnetic screening assay are re-exposed to the screening antibody, then incubated with a species-specific secondary antibody (antibody bound to antibody at bottom) conjugated to an enzyme (star-like structure). In some cases, on-bead peptoids or peptides isolated in the magnetic screening assay that retain bound screening antibody may be directly incubated with the secondary antibody without re-exposure to the screening antibody. When an appropriate color-changing substrate for the enzyme conjugated to the secondary antibody is added, complexes of on-bead peptoid or peptide, screening antibody, and secondary antibody will show a color change that is visible often by the naked eye and more clearly using a light microscope. For example, when the secondary antibody is conjugated to the enzyme horse radish peroxidase (HRP), adding the clear substrate 3,3',5,5'-tetramethylbenzidine (TMB) to complexes of on-bead peptoid, screening antibody, and secondary antibody will result in the formation of a blue product. The color intensity is directly proportional to the amount of secondary antibody present, which is proportional to the amount of screening antibody present, and therefore the presence of an on-bead ligand (the on-bead peptoid or peptide). By using these two sequential screening assays (magnetic and color screening), the number of false positives is greatly reduced. While the color screening can be replaced by other forms of testing, it is often helpful.

(FIG. 4A) Enzyme-linked immunosorbent assay (ELISA) comparing rabbit 12D pre-immunization serum (dotted lines) and post-immunization serum (solid lines) with affinity-purified RAR5A, shown in the FIGS. 4B-C. To affinity purify RAR5A, twenty-five milliliters of post-immunization serum from rabbit 12D, immunized with R5A-m-KLH adsorbed to alum, were passed repeatedly over a KLH-sepharose column to remove anti-KLH antibodies, as demonstrated in the FIG. 4B. The flow-through from this column was then passed over an R5A-SulfoLink column, which allowed the presentation of the R5A peptoid on the column resin without the maleimide linker used to conjugate the R5A peptoid to KLH, as shown in the FIGS. 4B-C. The affinity purified anti-R5A peptoid PAbs were eluted using 0.1 M glycine-HCl, pH 2.5 into tubes containing neutralization buffer (1 M Tris-HCl, pH 8.0) at 10% of the final volume. This R5A column eluate was immediately dialyzed into phosphate buffer saline (PBS) at pH 7.4 then concentrated using ammonium sulfate precipitation and centrifugal concentrator devices. For the enzyme linked immunoadsorbant assay (ELISA), triplicate wells of 96-well plates were coated for 2 hr at room temperature (RT) with 10 µg/mL of the following antigens: the R5A peptoid conjugated to a carrier protein irrelevant to the original immunization, bovine serum albumin (BSA) via maleimide chemistry (R5A-m-BSA; ●); an irrelevant peptoid conjugated to BSA via maleimide chemistry (RC-m-BSA; ▲); BSA alone (□); the immunogen, R5A-m-KLH (◆); KLH alone (◇); and an irrelevant protein, ovalbumin (OVA) (▽). Following washing with PBS, plates were blocked with Starting Block for 1 hour at RT, and then washed again with PBS. The indicated serum or R5A column eluate was then diluted from 1:1,000 to 1:1,000,000 in sample dilution buffer (1% Starting Block in PBS with 0.01% Tween 20 (PBST)) and applied to the plates for 1 hour at RT. Following washing using PBST, the plates were incubated with HRP-conjugated goat anti-rabbit IgG at a dilution of 1:2,500 in sample dilution buffer before the substrate TMB was applied. After 2 minutes the reaction was stopped by adding 2 M sulfuric acid ($H_2SO_4$) and the absorbance at 450 nm was recorded for each well using a plate reader. Data are displayed as the average of triplicate wells; error bars represent mean±standard deviation. Data shown represent one of three experiments performed. (FIG. 4D) Concentrated R5A column eluate (lane 1, both panels) was separated by sodium dodecyl sulfate polyacrylamide gel electrophoresis (SDS-PAGE) using a 4-15% gradient Phast-Gel under reducing conditions (left panel) and non-reducing conditions (right panel), then stained with Coomassie blue. Right panel, lane 2: low molecular weight marker. Left panel, lane 2: high molecular weight marker.

FIG. 6. GD12 MAb used for library screening binds specifically to both the PGD12.4 and PGD12.4L peptoids as determined in the ELISA using maleimide-activated plates. Duplicate wells of 96-wells maleimide-activated plates were first washed and after coated for 2 hours with recombinant ricin A chain (RiVax) (at 1 µg/mL), the PGD12.4 hit (at 50 μg/mL) and the PGD12.4L hit (at 50 μg/mL). The plates were washed out and followed by blocking with Staring Block for 1 hour at RT, and then washed. Primary MAb used for screening (mouse anti-ricin A chain, IgG1k, GD12 clone) (dark blue columns) and murine IgG1 isotypes (myeloma protein MOPC-21) (dark red columns) were added at a constant concentration of 1 μg/mL in sample dilution buffer for 1 hour at RT. For wells coated with PGD12.4 hit 14 different irrelevant mouse IgG MAbs were also added to separate wells (starting with the dark green column the MAbs used target the following human antigens: CD19, CD22, CD24, CD34, CD44, CD90, CD97, CD166, CD200, CD207, CD274, CD275, CD276, and CD277). Following washing, plates were incubated with the detection secondary antibody, a HRP-conjugated goat anti-mouse IgG at 1; 10,000 dilution in sample dilution buffer for 1 hour at RT. 3,3',5,5'-tetramethylbenzidine (TMB) was added followed by 2 M $H_2SO_4$ to stop the reaction. The absorbance at 450 nM was measured in a plate reader. This is one representative experiment out of four with similar results.

FIG. 7. PGD12.4 (A) and PGD12.4-L (B) peptoids preserve the reactivity to GD12 MAb upon conjugation to a carrier protein (BSA) via maleimide chemistry. Duplicate wells of 96-wells polystyrene ELISA plates were coated for 2 hours at RT with 10 μg/mL of the following antigens: RiVax (filled and open circles), PGD12.4 conjugated to maleimide-activated BSA (PGD12.4-m-BSA and PGD12.4L-m-BSA; filled and open squares), and an irrelevant peptoid, PR5A, conjugated to maleimide-activated BSA (PR5A-m-BSA; filled and open triangles). After washing, the plates were blocked with Staring Block overnight at 4° C., and then washed. The primary MAb used for screening (mouse anti-ricin A chain, GD12 clone) (all filled geometric shapes) and mouse IgG1 isotype-matched IgG1 (MOPC-21) (all open geometric shapes) were added at a range of concentrations from 10 to 0.05 μg/mL in sample dilution buffer for 1 hour at RT. Following washing, plates were incubated with the detection secondary antibody, a HRP-conjugated goat anti-mouse IgG at 1; 10,000 dilution in sample dilution buffer for 1 hour at RT. TMB was added and within 6-8 minutes the reaction was stopped by adding 2 M $H_2SO_4$. The absorbance at 450 nM was measured in a plate reader. This is one representative experiment out of four.

FIGS. 8A-B. GD12 MAb binds specifically to RiVax and PGD12.4-m-BSA conjugate as demonstrated by an indirect sandwich ELISA. (FIG. 8A) Duplicate wells of 96-wells polystyrene ELISA plates were coated for 2 hours at RT with RiVax at 10 μg/mL, then washed and blocked with Starting Block overnight at 4° C. After washing, the plate was divided into 3 parts and the following samples were added: GD12 MAb at a constant concentration of 1.5 μg/mL (filled triangles); PGD12.4-m-BSA conjugate at a concentration ranging from 0.0064 to 4.0 μg/mL (filled squares); and the mixtures of GD12 MAb at a constant concentration of 1.5 μg/mL and PGD12.4-m-BSA conjugate at concentrations ranging from 0.0064 to 4.0 μg/mL (filled circles). All reagents were added in sample dilution buffer for 1 hour at RT. Following washing, the plate was incubated with rabbit anti-BSA PAb at a constant concentration of 0.1 μg/mL in sample dilution buffer for 1 hour at RT. The, the plate was washed and a HRP-conjugated goat anti-rabbit IgG at 1; 10,000 dilution in sample dilution buffer was added for 1 hour at RT. TMB was used followed by 2 M $H_2SO_4$ to stop the reaction. The absorbance at 450 nM was measured in a plate reader. This is one experiment out of two performed (FIG. 8B).

DESCRIPTION OF ILLUSTRATIVE EMBODIMENTS

The inventors propose methods for screening libraries of peptoids or related compounds using MAbs known to neutralize pathogens or toxins, inactivate prions, or inhibit the growth of cancer cells. The selected peptoids are conjugated to carrier proteins, formulated into vaccines and used to elicit protective antibodies in animals. For each vaccine, the particulars of the screen will differ depending upon the nature of the antigen. However, all will have in common a design that is optimized to select those peptoids or related compounds by known protective MAbs or pools of said MAbs that can select the binding peptoid(s). A key issue will be to identify B cell epitopes that are conserved among different strains of a pathogen or critical for the function of a toxin. This structure does not have to be known in advance, so that the screen is unbiased. This can be done if the antibody used for selection of a peptoid recognizes a broadly conserved structure on the pathogen/toxin/prion that inactivates the pathogen, prion, toxin, etc. It might also be done by using cocktails of MAbs that recognize epitopes on several related pathogens. Peptoids or related compounds need not resemble a natural epitope in their primary, secondary or tertiary structure, but must only appear similar in shape "as viewed by" the combining site of an antibody. Finally, important epitopes on pathogens are not always immunogenic, because they have a low copy number, are buried in the membrane of the pathogen, and are highly conformational. These may be poorly recognized by receptors on critical B cells clones or the virgin B cell clones might be tolerant because of cross-reactivity with self-antigen. In the case of peptoid mimetics, they can be selected by a known protective MAb, and presented in a high copy number when coupled to a carrier protein that will induce robust T cell help. Since peptoids are mimetic structures, the copy number and availability of whatever they recognize on the native pathogen should be irrelevant, as long as the correct screening MAb is used. Hence, when present in high copy numbers on a carrier, peptoids should be very immunogenic for certain B cell clones and elicit high antibody titers. This should occur because they are presented in a multivalent and available array on a carrier protein that has numerous T cell epitopes. Furthermore, their inherent protease resistance should facilitate the maintenance of their native structure in the blood and lymphoid organs so that they are recognized by the antigen-specific receptors on the "right" non-self-reactive B cells in the lymphoid tissues due to a "shape" that has not been destroyed by proteases. These and other aspects of the invention are set forth in detail below.

I. Definitions

The phrases "isolated" or "biologically pure" refer to material that is substantially or essentially free from other like components, as well as other non-related materials. Thus, an isolated peptoid in accordance with the invention preferably does not contain measurable amounts of other dissimilar peptoids or other biological materials to which the peptoid is not covalently linked.

The term "hapten" relates to a small molecular structure that is capable of binding to an immune receptor that is usually a B cell receptor, but, by itself, cannot elicit an immune response. Rather, a hapten can only elicit an immune response when attached to a larger molecule such as a carrier protein that will stimulate T cells. A hapten can sometimes induce an IgM response if coupled to a B cell mitogen, a nanoparticle, liposome of molecule such as ficoll. In the art, these are known as T-independent antigens. These IgM responses rarely affinity mature or do so poorly with boosting, are short lived and do not usually isotype class switch.

An "epitope" is defined as an antigenic determinant that is a part of an antigen that is recognized by the immune system, specifically by antibodies, or receptors on B cells, or T cells. Although epitopes are usually non-self proteins, sequences derived from the host that can be recognized by the host's immune system are also epitopes. The epitopes of protein antigens are divided into two categories, conformational epitopes and linear epitopes. A conformational epitope is composed of discontinuous sections of the antigen's amino acid sequence and rely on shape or tertiary structure of the antigen. Most B cell epitopes are conformational. In contrast T cell epitopes are linear peptides presented in the grooves of HLA antigens or glycolipids presented in CD molecules on APCs. The peptides are usually derived from the carrier protein to which the B cell epitope is bound.

A "protective immune response" or "protective antibody" refers to an immune response or antibody that is able to prevent or reduce disease symptoms or progression.

A "broadly protective" antibody reacts with and inhibits a pathogen or disease-causing agent regardless of natural antigenic variation in the pathogen or agent.

II. Peptoid Libraries

A. Peptoid Synthesis

As will be described below, the present invention relies, in part, on peptoids and related compounds, such as "hybrid" molecules containing D-amino acids, and their use in the creation of synthetic mimics of native B cell epitopes. Therefore, a review of the chemical and biological properties of these molecules is relevant.

Figure 1C:
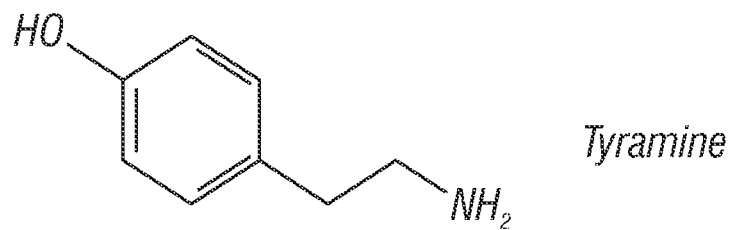
Figure 1C:
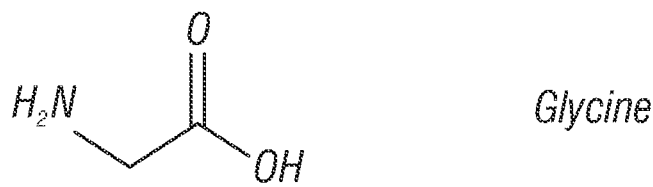
Figure 1C:
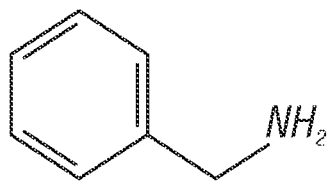
Figure 1C:
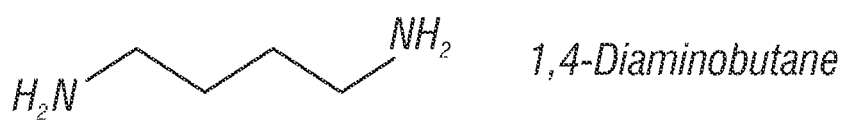
Figure 1C:
Figure 1C:
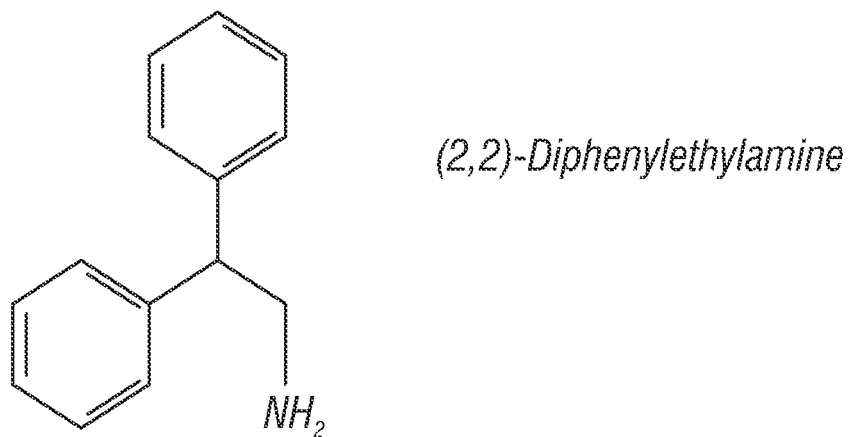
Figure 1C:
Figure 1C:
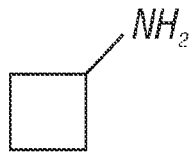
Figure 1C:
Figure 1C:
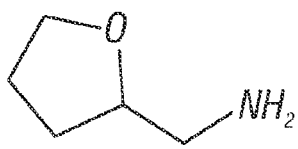
Figure 1C:
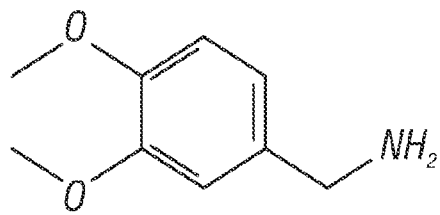
Figure 1C:
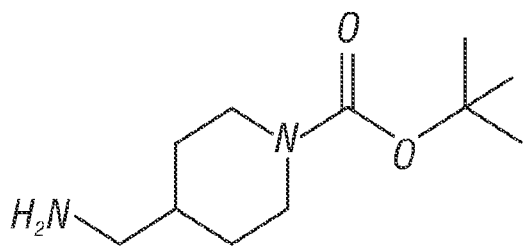
Figure 1C:
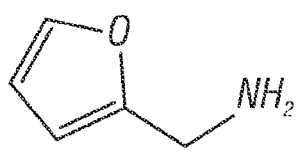
Figure 1C:
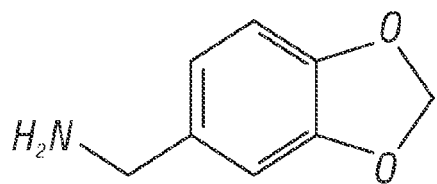
Figure 1C:
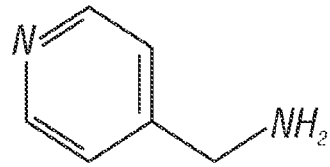
Figure 1C:
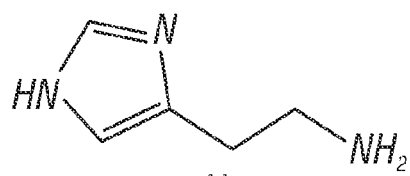
Figure 1C:
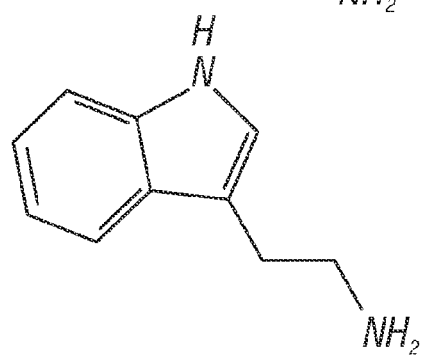
Figure 1C:
Figure 1C:
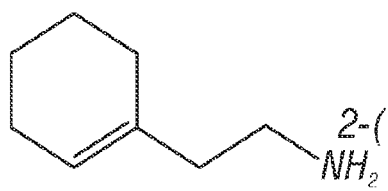
Figure 1C:
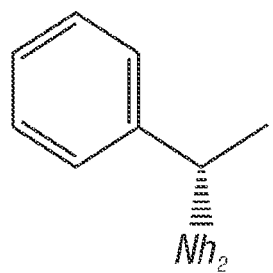

Peptoids (Simon et al., 1992) are oligomers of N-substituted glycines (see FIGS. 1A-C). Despite the structural similarity between peptides and peptoids, peptoids are quite different from peptides in several important ways (FIG. 1A). First, and very importantly for antibody-inducing vaccines based on B cell epitopes, they are completely resistant to natural proteases. This is the case because in peptoids, as compared to peptides, the side chain (R group) reside on the nitrogen rather than the chiral carbon atoms. This modification, which displays the peptoid R group in a planar presentation, produces a misalignment of the side chains and the carbonyl groups such that the susceptible (amide) bond is out of range of the nucleophilic catalysts at protease active sites, and hence, not cleavable (Miller and Moos, 1994).

Secondly, peptoids are far easier to synthesize than peptides, at least with respect to making compounds with "unnatural" side chains. The α-amino acids that make up peptides are chiral (optically active) molecules. If unnatural amino acids are to be incorporated into peptides, one must carry out sometimes difficult and expensive syntheses of these building blocks. Peptoids lack chiral centers since the substitution is on the nitrogen atom rather than the α-carbon. This allows peptoids to be made using the so-called "sub-monomer" route. As shown, the side chain is derived from a simple primary amine, hundreds of which can be purchased inexpensively. It is important to note that peptoids are not restricted to the 20 known natural amino acids, while peptides are. Hence, any amine can be attached to the nitrogen and the diversity of oligo-peptoids is therefore enormous. Currently, theoretical diversity can be as high as $10^{10}$.

The inventors propose the use of chemical diversity in combinatorial libraries whose design can incorporate a structural understanding of neutralizing epitopes, although this is not necessary. A series of chemically-diverse one-bead-one-compound peptoid combinatorial libraries can be created. These libraries will widely sample chemical space in an effort to identify high quality epitope mimics and will include a broad range of hydrophilic, hydrophobic, aromatic, heteroaromatic, and charged side-chains (Butterfoss et al., 2012). These libraries will contain linear, hybrid peptide/peptoid, cyclic peptoid, turn mimic, or other conformationally constrained peptoid designs. They will be synthesized by automated mix and split solid phase combinatorial synthesis on hydrophilic macrobeads and contain $10^5$ to $10^{10}$ theoretical compounds each.

The inventors can synthesize and screen large combinatorial libraries of synthetic peptoids (Figliozzi et al., 1996). They and their collaborators have also utilized custom robotic synthesizers that have been optimized over several generations to perform the fully automated synthesis of peptoids polymers, although polymers can still be made by hand and still are. Individual compounds can be prepared in parallel, or combinatorial libraries of high complexity can be prepared. The automated two-step submonomer cycle takes <30 minutes, so that the synthesis of a 30 residue peptoid can be synthesized overnight. 'Mix and split' combinatorial synthesis allows a very large number of different sequences to be synthesized simultaneously (Lam et al., 1991; Lam et al., 1997; Yu et al., 2005; Zuckermann et al., 1994), in such a fashion that each resin bead in the combinatorial library contains a single compound (Lam et al., 1991; Lam et al., 1997). This means that one can generate millions of peptoid oligomers in a single robotic run. Cyclic peptoid libraries can readily be synthesized by on-resin macrocyclization of linear peptoids in high yield by known methods (Kwon et al., 2008; Lee et al., 2010).

The key to the design of cyclic peptoid libraries is the need to determine the sequence of the antibody-bound peptoids or "hits" after screening a one-bead-one compound library. Cyclic peptoids lack a free N-terminus and preclude Edman sequencing. While peptoids can be sequenced by MS/MS, cyclic molecules will fragment at multiple positions, complicating interpretation of the MS/MS spectrum. One solution to this problem is to employ a cleavable scaffold strategy that will linearize the cyclic peptoid prior to sequencing (Lee el al., 2010; Simpson & Kodadek, 2012). An alternative method is a "two compound, one bead" approach in which each bead contains both a linear and cyclic molecule containing the same peptide sequence (Joo et al., 2006). This is possible using segregated bi-functional beads with orthogonal linkers (Liu et al., 2002). The cyclic bead can be displayed on the bead surface and cleaved for secondary in-solution screening while the linear peptoid remains attached on the bead for later sequencing. Additionally the linker region can incorporate functionality that will allow for the on-bead fluorescent labeling of peptoids supporting secondary screening (Hintersteiner et al., 2009).

In contrast to pure peptoids, "hybrids" are molecules consisting of both N-substituted monomers (peptoids) and peptide monomers (D- or L-peptides). While peptoid monomers are proteolytically stable and available by the hundreds, there are some advantages to including peptide monomers. Both D- and L-peptide monomers can be incorporated into the backbone, although L peptides are proteolytically unstable, making them poor candidates for a vaccine antigen. D-peptides are peptides synthesized from N-terminus to C-terminus just like L peptides, but with monomers of an opposite chirality. D-peptides are proteolytically stable, as natural proteases are stereospecific and unable to cleave the peptide bond in the D analog (Nair et al., 2003). An overlap of D-peptides and peptoids would reveal overlapping backbone structure, but R groups, which are planar in the peptoid, are not planar in the D-peptide. Thus, the incorporation of D-peptides introduces chirality to the otherwise planar peptoid side groups. Furthermore, D-peptides introduce stability to the otherwise 'floppy' peptoid. D-peptides are energetically favored in the trans conformation, making them less floppy and more stable (adding similar advantages as the cyclic peptides by increasing backbone rigidity). These hybrid D-peptide/peptoid compounds can be synthesized by incorporating well developed peptide synthesis protocols into the submonomer peptoid synthesis protocols. The D-peptide monomers are merely more shapes added to the library. A summary of the characteristics of the various monomers that can be used to create peptoids and related compounds is illustrated in TABLE 1 below.

TABLE 1

Characteristics of Monomers

| Characteristics | L-Peptide | D-Peptide | Peptoid | Hybrid | Cyclic |
|---|---|---|---|---|---|
| Monomer diversity | 20 | 20 | Hundreds | Hundreds | Hundreds |
| Proteolytic stability | No | Yes | Yes | Yes | Yes |
| Cost | High | High | Low | Low-Medium | Low |
| Shapes | Few | Few | Many | Many | Many |
| Flexibility | Low | Low | High | Low-High | Low |

It has been reported that the synthesis of peptoid libraries containing enormous diversity can be made (Alluri et al., 2003). In addition more complex cyclic peptoids are also under development. A useful feature of peptoids and peptide-peptoid hybrids is that they can be sequenced by the same technology employed to sequence peptides (Alluri et al., 2003; Boeijen and Liskamp, 1998; Paulick et al., 2006). For example, a single bead from a library synthesis can be placed into an automated Edman sequencer and the sequence of the peptoid or related compound determined. Alternatively, if the peptoid or related compound can be cleaved from the bead and its structure can be deduced from MS/MS.

A second important point for the application of peptoids and related compounds to the invention is the variety of ways with which screening can be accomplished. For example, this can be done by screening bead-displayed libraries or by arraying part of the library on chemically-modified glass microscope slides or by a combination of the two methods. The technology was shown and described in detail by Reddy and Kodadek (2005).

Peptoid libraries have been proven to be rich sources of ligands for a variety of different proteins (Alluri et al., 2006; Alluri et al., 2003; Heizmann et al., 1999; Lim et al., 2007; Nguyen et al., 2000; Xiao et al., 2007; Zuckermann et al., 1994). The inventors use reproducible and validated protocols with which to screen large peptoid libraries displayed on polystyrene beads (TentaGel, Rink Amide) coupled to (or not) a hydrophilic linker. The TentaGel resins are grafted copolymers consisting of a cross-linked polystyrene matrix on which polyethylene glycol (PEG) is grafted. This bead type is non-cleavable; indicating that the sequences built on them cannot be cleaved off Rink Amide beads are polystyrene beads with an amide linker that allows for cleavage. However, the conditions under which the peptoid side groups are cleaved off the sequence, 95% trifluoroaceteic acid (TFA), also cleave the sequence from the bead, making them poor options for library screening. To address the need for a cleavable linker on TentaGel beads, the inventors can incorporate one of two kinds of cleavable linkers at the beginning of all library synthesis: a proline-aspartic acid-cysteine linker that can be cleaved by 94-97.5% TFA (depending of the chemical structure), or a methionine linker that can be cleaved by a 0.1M cyanogen bromide solution. These linkers enable one to screen peptoid libraries 'on beads' and then remove compounds from the selected beads using cleaving solutions.

An illustrative example is a published protocol employed to obtain a peptoid inhibitor of the proteasome 19S regulatory particle of the 26S proteasome (Lim et al., 2007). The library was screened for peptoids that bind to a FLAG peptide-epitope-tagged yeast proteasome. Since binding was to be detected by an indirect fluorescent immunoassay, the library was first pre-screened to clear it of compounds that bound directly to the antibodies and other detection agents to be employed. The beads were then incubated with a yeast whole cell extract obtained from cells expressing epitope-tagged proteasomes. "Hits" (beads bound by antibody) were visualized by incubating them with an anti-FLAG antibody, a biotinylated secondary antibody and red-emitting streptavidin-coated quantum dot. Beads with a red halo, indicative of retention of the quantum dot, were collected and the peptoids on those beads were sequenced. This resulted in the isolation of the desired peptoids. Note that this work and other published examples (Alluri et al., 2003; Alluri et al., 2006; Reddy et al., 2004; Xiao et al., 2007) demonstrate the ability to identify library-encoded peptoids that bind a low level of a particular target protein in a complex mixture containing thousands of different proteins. This capability, employed in a somewhat different context, is a key part of the invention.

Peptoids and related compounds represent a new universe of "shapes" which, like haptens, can be recognized by antibodies. There have been several reports of peptoids that bind to antibodies. In one case, Hoffmann et al. (2006) used a stepwise approach to derive a peptoid mimic from an antibody-binding peptide that bound the same antibody with only an 8-fold reduced affinity compared to the peptide. In the other, a small array of peptoids synthesized on a cellulose membrane was probed with a MAb and it was shown that some of the spots on the array retained the antibody (Heine et al., 2003). The putative peptoid-antibody complexes were not characterized further. In more recent work published by Moola et al. (2011) it has been demonstrated that peptoid microarrays are capable of retaining IgG antibodies from whole serum.

There has been one report of a peptoid that bound an antibody that also recognizes a linear peptide (Hoffmann et al. 2006). This peptoid was obtained not by screening a library per se, but by substitution analysis in which each position of the peptide was replaced by a set of different peptoid building blocks resulting in a small array. After probing the array for antibody binding, the best binding peptide-peptoid hybrids were selected and subjected to a successive transformation. In this stepwise fashion, they were able to eventually "morph" the peptide into a peptoid that was still recognized by the antibody with an affinity only eight-fold reduced relative to that of the peptide. However, this would not be considered demonstrative of the ability to use a peptoid, selected from a random library, to mimic a three-dimensional, non-contiguous protein epitope, much less prove that immunization with a peptoid selected by a particular antibody could elicit an antibody response against the native protein or peptide. To the best of the inventors' knowledge, there has been no demonstration that peptoids can mimic B cell epitopes much less that can be attached to carrier proteins and used in a vaccine that will protect against a dangerous substance such as a toxin or a disease causing entity such as a pathogen or prion. Nor has there been any demonstration of peptoid-mimetics of cancer antigens.

B. Surfaces

Members of a peptoid library are often "arrayed" on a surface that permits one to reference a given peptoid by its relative location. Typical "arrays" include glass plates, chips and beads. Given that a larger number of peptoids in library provides a better opportunity to identify useful B cell epitope mimics, a particularly useful embodiment will involve the linking of peptoids to beads given the extremely large number of peptoids that can be screen simultaneously using this format.

A large number of commercially available beads are described that will be suitable for screening peptoid libraries according to the present invention. Such beads can be formed from metals (e.g., zinc, gold), polymers (e.g., latex) resins, (e.g., TentaGel®), or glass. For example, Luminex (Austin Tex.) is a world leader in the development of bead technologies and provides a variety of options including high throughput analyticals, bead coding and surface modifications.

C. Variants of Peptoids

It is contemplated that peptoids of the present invention, once selected, may be further modified to improve their reactivity with the selecting antibody and/or to improve their ability to elicit a protective immune response when administered to a vertebrate. It also will be understood that additional peptoid monomers may be included at the N- or C-terminus of a selected peptoid to as to improve stability or immunogenicity or to facilitate conjugation to a carrier or surface.

D. Isolation of Antibody-Binding Peptoids.

It may be desirable to isolate ("purify") peptoids away from a larger library of peptoids, or from a selecting antibody after binding. The term "purified peptoid" as used herein, is intended to refer to a composition, isolatable from other components, wherein the peptoid is purified to any degree relative to a prior state.

III. Infectious Disease Agents And Toxins

The following is an exemplary but non-limiting discussion of various disease agents that could be the subject of vaccine development in accordance with the present invention.

A. Bacterial Pathogens

There are hundreds of bacterial pathogens in both the Gram-positive and Gram-negative families that cause significant illness and mortality around the word, despite decades of effort developing antibiotic agents. Indeed, antibiotic resistance is a growing problem in bacterial disease.

One of the bacterial diseases with highest disease burden is tuberculosis, caused by the bacterium *Mycobacterium tuberculosis*, which kills about 2 million people a year, mostly in sub-Saharan Africa. Pathogenic bacteria contribute to other globally important diseases, such as pneumonia, which can be caused by bacteria such as *Streptococcus* and *Pseudomonas*, and food borne illnesses, which can be caused by bacteria such as *Shigella, Campylobacter*, and *Salmonella*. Pathogenic bacteria also cause infections such as tetanus, typhoid fever, diphtheria, syphilis, and leprosy.

Conditionally pathogenic bacteria are only pathogenic under certain conditions, such as a wound facilitates entry of bacteria into the blood, or a decrease in immune function. For example, *Staphylococcus* or *Streptococcus* are also part of the normal human flora and usually exist on the skin or in the nose without causing disease, but can potentially cause skin infections, pneumonia, meningitis, and even overwhelming sepsis, a systemic inflammatory response producing shock, massive vasodilation and death. Some species of bacteria, such as *Pseudomonas aeruginosa*, *Burkholderia cenocepacia*, and *Mycobacterium avium*, are opportunistic pathogens and cause disease mainly in people suffering from immunosuppression or cystic fibrosis.

Other bacterial invariably cause disease in humans, such as obligate intracellular parasites (e.g., *Chlamydophila*, *Ehrlichia*, *Rickettsia*) that are capable of growing and reproducing only within the cells of other organisms. Still, infections with intracellular bacteria may be asymptomatic, such as during the incubation period. An example of intracellular bacteria is *Rickettsia*. One species of *Rickettsia* causes typhus, while another causes Rocky Mountain spotted fever. *Chlamydia*, another phylum of obligate intracellular parasites, contains species that can cause pneumonia or urinary tract infection and may be involved in coronary heart disease. *Mycobacterium*, *Brucella*, *Francisella*, *Legionella*, and *Listeria* can exist intracellular, though they are facultative (not obligate) intracellular parasites.

Gram-positive bacteria include *Staphylococcus aureus*; *Staphylococcus epidermidis*; *Staphylococcus saprophyticus*; *Streptococcus pyogenes* (Lancefield group A, beta-hemolytic); *Streptococcus agalactiae* (Lancefield group B, beta-hemolytic); *Streptococcus* Viridans group (most are alpha-hemolytic) including, for example, the Mitus group (*S. mitus*, *S. sanguis*, *S. parasanguis*, *S. gordonii*, *S. crista*, *S. infantis*, *S. oralis*, *S. peroris*), the *Salivarius* group (*S. salivarius*, *S. vestibularis*, *S. thermophilus*), the *Mutans* group (*S. mutans*, *S. sobrinus*, *S. criceti*, *S. rattus*, *S. downei*, *S. macacae*), and the *Anginosus* group (*S. anginosus*, *S. constellatus*, *S. intermedius*); *Streptococcus*, e.g., *S. bovis*, *S. equinus* (Lancefield group D, alpha-hemolytic); Streptococcuspneumoniae (no Lancefield antigen; alpha-hemolytic); *Peptostreptococcus* and *Peptococcus*; *Entercoccus faecalis*; *Enterococcus faeccium*; *Cornybacterium diphtheria*; *Bacillus anthracis*; *Bacillus cereus*; *Clostridium C. botulinum* (more rarely, *C. baratii* and *C. butyricum*); *Clostridium tetani*; *Clostridium perfringens*; *Clostridium difficile*; *Clostridium sordellii*; *Listeria monocytogenes*; *Actinomyces israelii*; *Nocardia asteroids*; *Streptomyces*.

Gram-negative bacteria include *Neisseria meningitides*; *Neisseria gonorrhoeae*; *Moraxella* (subgenera *Branhamella*) *catarrhalis*; *Kingella* (most commonly kingae); *Acinetobacter baumannii*, *Oligella ureolytica*; *Oligella urethralis*; *Escherichia coli*; *Shigella* (*S. dysenteriae*, *S. flexneri*, *S. boydii*, *S. sonnei*); *Salmonella* non typhoidal, including *S. enterica* serotype *enteritidis*, *S. enterica* serotype *typhimurium*, *S. enterica* serotype *Choleraesuis*, *S. bongori*, *Salmonella S. enterica* serotype *Typhi*; *Yersinia enterocolitica*, *Klebsiella pneumoniae*; *Proteus mirabilis*; *Enterobacter*; Cronobacter (formerly called *Enterobacter sakazakii*); *Serratia*; *Edwardsiella*; *Citrobacter*; *Hafnia*; *Providencia*; *Vibrio cholera*; *Vibrio parahemolyticus*; *Campylobacter*; *Helicobacter* (formerly called *Campylobacter*) *pylori*, *Pseudomonas aeruginosa*; *Burkholderia cepacia*; *Burkholderia mallei*; *Burkholderia pseudomallei*; *Stenotrophomonas maltophilia*; *Bacteroides fragilis*, *Bacteroides melaninogenicus*; *Fusobacterium*; *Haemophilus influenza*; *Haemophilus ducreyi*; *Gardnerella* (formerly called *Haemophilus*) *vaginalis*; *Bordetella pertussis*; *Legionella*; *Yersinia pestis*; *Francisella tularensis*; *Brucella B. melitensis* (infects sheep/goats); *B. abortus* (abortions in cows); *B. suis* (pigs); *B. canis* (dogs); *B. maris* (marine animals); *Pasteurella multocida*; *Streptobacillus moniliformis*; *Spirillum minus*; *Treponema pallidum*, *Treponema pallidum* subspecies *pertenue*; *Treponema pallidum* subspecies *endemicum*; *Treponema pallidum* subspecies *carateum*; *Borrelia burgdorferi*; *Borrelia*; *Leptospira*; *Chlamydia trachomatis*; *Chlamydia pneumonia*; *Chlamydia psittaci*; *Rickettsiae rickettsia*; *Rickettsiae akari*; *Rickettsiae prowazekii*; *Rickettsiae typhi*; *Rickettsiae tsutsugamushi*; *Rickettsiae parkeri*; *Rickettsiae africae*; *Rickettsia conorii*; *Rickettsia australis*; *Rickettsia siberica*; *Rickettsia japonica*; *Bartonella Quintana*; *Bartonella henselae*; *Bartonella bacilliformis*; *Coxiella burnetii*; *Ehrlichia*; *Anaplasma phagocytophilum*; *Neorickettsia*; *Orientia*; *Klebsiella granulomatis* (formerly called *Calymmatobacterium granulomatis*); *Capnocytophaga*.

Other bacteria include *Mycobacterium tuberculosis*; *Mycobacterium bovis*; *Mycobacterium leprae*; *Mycobacterium avium-intracellulare* or *avium* complex (MAI or MAC); *Mycobacterium ulcerans*; *Mycobacterium kansasii*; *Mycobacterium marinum*; *Mycobacterium scrofulaceum*; *Mycobacterium fortuitum*; *Mycobacterium chelonei*; *Mycobacterium abscessus*; *Mycoplasma pneumonia*; *Ureaplasma urealyticum*.

B. Viral Pathogens

Vaccines may be developed for any viral pathogen for which protective antibodies are available. Viruses include DNA and RNA viruses. These include respiratory viruses such as Adenoviruses, Avian influenza, Influenza virus type A, Influenza virus type B, Measles, Parainfluenza virus, Respiratory syncytial virus (RSV), Rhinoviruses, and SARS coronavirus, gastro-enteric viruses such as Coxsackie viruses, enteroviruses such as Poliovirus and Rotavirus, hepatitis viruses such as Hepatitis B virus, Hepatitis C virus, Bovine viral diarrhea virus (surrogate), herpes viruses such as Herpes simplex 1, Herpes simplex 2, Human cytomegalovirus, and Varicella zoster virus, retroviruses such as Human immunodeficiency virus 1 (HIV-1), and Human immunodeficiency virus 2 (HIV-2), as well as Dengue virus, Hantavirus, Hemorrhagic fever viruses, Lymphocytic choriomeningitis virus, Smallpox virus, Ebola virus, Rabies virus, West Nile virus (WNV) and Yellow fever virus.

Examples of viruses include Parvoviridae; Papovaviridae (Human papilloma virus (HPV); BK polyomavirus; JC polyomavirus); Adenoviridae (Adenovirus, types 40 and 41); Herpesviridae (simplex virus type 1 (HHV-1); Herpes simplex virus type 2 (HHV-2); Macacine herpesvirus 1; Varicella-zoster virus (VZV; HHV-3); Epstein-Barr virus (EBV; HHV-4); Cytomegalovirus (CMV; HHV-5); Human Herpesvirus 6 (HHV-6); HHV-7; Kaposi's sarcoma-associated herpesvirus (HHV-8); Hepadnaviridae (Hepatitis B virus); Poxviridae (Smallpox (Variola major); Alastrim (Variola minor); Vaccinia; Cowpox; Monkeypox; Goat pox, pseudocowpox virus, bovine papular stomatitis virus, tanapox, volepox and related pox viruses such as avipox, buffalopox, racoonpox, squirrelpox, etc.); Molluscum contagiosum; Picornaviridae (Polio virus; Coxsackie A virus; Coxsackie B; virus; Foot and mouth disease; ECHO virus; Hepatitis A virus; Rhinovirus); Astroviridae; Caliciviridae (Norwalk virus; Norovirus; Sapoviruses; Hepatitis E virus); Reoviridae (Rotavirus); Togaviridae (Alpha viruses; Western equine encephalitis (WEE) virus; Eastern equine encephalitis (EEE) virus; Venezuelan equine encephalitis (VEE) virus; Chikungunya virus; Rubivirus (rubella)); Flaviviridae (Yellow fever virus; Dengue virus; St. Louis encephalitis virus; Japanese encephalitis virus; Tick-borne encephalitis virus; Omsk hemorrhagic fever virus; Al Khumra virus; Kyasanur Forest disease virus; Louping ill virus; West Nile virus; Kunjin virus; Murray Valley fever virus; Powassan virus; Hepatitis C virus; Hepatitis G virus); Coronoviridae (Respiratory illness (cold); Severe Acute Respiratory Syndrom)-corona virus (SARS-CoV)); Bunyaviridae (California encephalitis virus; La Crosse virus; Rift Valley fever virus; Phleboviruses; Sandfly fever virus; Nairovirus; Hantavirus); Orthomyxoviridae (Influenza virus (types A, B & C); Paramyxoviridae (Parainfluenza virus; Respiratory syncytial virus (RSV); Hendra virus disease (formerly equine morbillivirus); Nipah virus encephalitis; Mumps Measles; Newcastle disease virus); Rhabdoviridae (Rabies virus); Filoviridae (Marburg virus (acute hemorrhagic fever); Ebola virus (acute hemorrhagic fever)); Arenaviridae (Lymphocytic choriomeningitis virus; Lassa fever virus; Lujo virus; Chapare virus; Junin virus; Machupo virus; Guanarito virus; Sabia virus); Retroviridae (Human Immunodeficiency virus (HIV) types I and II; Human T-cell leukemia virus (HLTV) type I; Human T-cell leukemia virus (HLTV) type II; Spumaviruses; Xenotropic murine leukemia virus-related (XMRV).

C. Fungal Pathogens

Pathogenic fungi are fungi that cause disease in humans or other organisms. The following are but a few examples.

*Candida* species are important human pathogens that are best known for causing opportunist infections in immunocompromised hosts (e.g., transplant patients, AIDS sufferers, and cancer patients). Infections are difficult to treat and can be very serious. *Aspergillus* can and does cause disease in three major ways: through the production of mycotoxins; through induction of allergenic responses; and through localized or systemic infections. With the latter two categories, the immune status of the host is pivotal. The most common pathogenic species are *Aspergillus fumigatus* and *Aspergillus flavus*. *Cryptococcus neoformans* can cause a severe form of meningitis and meningo-encephalitis in patients with HIV infection and AIDS. The majority of *Cryptococcus* species lives in the soil and do not cause disease in humans. *Cryptococcus laurentii* and *Cryptococcus albidus* have been known to occasionally cause moderate-to-severe disease in human patients with compromised immunity. *Cryptococcus gattii* is endemic to tropical parts of the continent of Africa and Australia and can cause disease in non-immunocompromised people. *Histoplasma capsulatum* can cause histoplasmosis in humans, dogs and cats. *Pneumocystis jirovecii* (or *Pneumocystis carinii*) can cause a form of pneumonia in people with weakened immune systems, such as premature children, the elderly, transplant patients and AIDS patients. *Stachybotrys chartarum* or "black mold" can cause respiratory damage and severe headaches. It frequently occurs in houses in regions that are chronically damp.

Examples include *Malassezia furfur; Exophiala werneckii; Microsporum* species; *Trichophyton* species; *Epidermophyton floccosum; Sporothrix schenckii; Phialophora verrucosa; Cladosporium carrinonii; Fonsecaea* species; *Coccidioides; Histoplasma capsulatum; Blastomyces dermatitidis; Cryptococcus neoformans; Cryptococcus gattii; Candida albicans; Aspergillus fumigatus; Aspergillus flavus; Aspergillus niger; Rhizopus; Rhizomucor; Mucor; Exserohilum*.

D. Parasites

Parasite presents a major health issue, particularly in under-developed countries around the world. Significant pathogenic parasites include worms (roundworms, flatworms) and protozoa. *Entamoeba histolytica; Giardia lamblia; Trichomonas vaginalis; Plasmodium falciparum; Plasmodium malariae; Plasmodium ovale; Plasmodium vivax; Trypanosoma cruzi; Ascaris lumbricoides; Trichinella spiralis; Toxoplasma gondii; Leishmania donovani; Leishmania tropica; Leishmania braziliensis; Schistosoma mansoni; Schistosoma japonicum; Schistosoma haematobium; Cyclospora cayetanesis; Crytosporidium*, e.g., *C. parvum, C. hominis; Cystoisospora* species (formerly called *Isospora* species), e.g., *C. belli; Naegleria fowleri; Acanthamoeba* species; *Sappinia diploidea; Sappinia pedata; Balamuthia mandrillaris; Pneumocystis jiroveci* (formerly called *Pneumocystis carinii*); *Plasmodium knowlesi; Babesia microti; Babesia divergens; Babesia duncani; Babesia* (no species name yet but designated MO-1); *Trypanosoma brucei rhodesiense; Trypanosoma brucei gambiense; Balantidium coli; Dientamoeba fragilis;* Phylum: Microsporidia; *Sarcocystis; Baylisascaris; Necator americanus; Ancylostoma duodenale; Strongloides stercoralis; Trichinella pseudospiralis; Trichinella nelsoni; Trichinella britovi; Trichinella nativa; Trichuris trichiura; Enterobius vermicularis; Anisakis simplex; Pseudoterranova decipiens; Trichostrongylus; Oesophagostomum*, e.g., *O. bifurcom; Angiostrongylus; Capillaria; Dirofilaria; Loa boa; Onchocerca volvulus; Wuchereria bancrofti; Brugia malayi; Brugia timori; Mansonella, M. perstans; M. streptocerca; M. ozzardi; Dracunculus mediensis;* Cutaneous larva migrans (commonly *Ancylostoma braziliense*=dog hookworm; also *A. caninum, A. ceylanicum*, and *Uncinaria stenocephala*); Visceral larva migrans (most commonly *Toxocara canis*=dog roundworm, less commonly *Toxocara cati*=cat roundworm, *Baylisascaris procyonis*=raccoon roundworm) or ocular larva migrans or neural larva migrans (*B. procyonis*); *Gnathostoma G. spinigerum* and *G. hispidum; Dicrocoelium dendriticum; Echinostoma*, e.g., *E. hortense, E. macrorchis, E. revolutum, E. ilocanu*, and *E. perfoliatum; Thelazia; Shistosoma japonicum; Shistosoma mansoni; Shistosoma haematobium; Shistosoma intercalatum; Shistosoma mekongi; Austrobilharzia variglandis* and other schistosomes; *Taenia solium; Taenia saginata; Taenia multiceps; Taenia serialis; Taenia asiatica; Diphyllobothrium latum; Hymenolepis nana; Echinoccoccus; Paragonimus; Clonorchis sinensis; Dipylidium caninum; Fasciola, F. hepatica; F. gigantica; Fasciolopsis buski; Heterophyes heterophyes; Hymenolepsis, H. nana, H. dimnuta; Opisthorchis; Bertiella*, e.g., *B. studeri* and *B. mucronata; Macracanthorhynchus hirudinaceous; Moniliformis moniliformis; Bolbosoma* species; *Metagonimus yokogawai; Dioctophyme renale; Mesocestoides*, e.g., *M. lineatus* and *M. variabilis; Philophthalmus*, e.g., *P. lacrymosus, P. gralli, P. palpebrarum; Spirometra*, e.g., *S. mansoni, S. ranarum, S. mansonoides, S. erinacei; Sparganum proliferum*.

E. Toxins

Toxins constitute a significant threat to the population in both developed and under-developed countries. Biotoxins are biological in nature, i.e., they are produced by many living organisms, including bacteria, insects, snakes and plants. These include a wide variety of insect toxins, such as spider, scorpion, bee wasp, or ants, snake toxins, many of which are neurotoxins to hemotoxins, cyanotoxins, jellyfish toxins, ricin toxin, botulism toxin, tetanus toxin and mycotoxins.

Environmental toxins, on the other hand, are toxins that are non-biological in origin, and can be natural or manmade. These include industrial and agricultural chemicals such as phthalates, polychlorinated biphenyls (PCBs), pesticides, dioxin, asbestos, chlorine, chloroform, volatile organic compounds (VOCs), and heavy metals such as lead, cadmium and arsenic.

F. Other Agents

A variety of other agents may be subject to vaccines developed in accordance with the present invention. For example, antibodies to prions (proteinaceous infectious particles) that can give rise to diseases such as mad cow and Kuru can be used to screen the peptoid libraries. Also, small insects that embed themselves in the skin such as ticks, bed bugs or lice can be subject to a host immune response. The following are such agents or diseases: Kuru; Creuzfeldt-Jakob Disease; Fatal familial insomnia; Gerstmann-Straussler-Scheinker disease; Scrapie; Bovine spongiform encephalopathy (BSE; mad cow disease); scabies (human itch mite); lice; bed bugs; maggots; chigoe flea (*Tunga penetrans*); *Blastocystis hominis*.

IV. Screening

The inventors propose a method of selecting peptoid mimetics using MAbs to screen libraries of peptoids in order to identify peptoids or related compounds that serve as B cell epitope mimics. The use of a broadly protective MAb, or a pool of such MAbs, facilitates the selection of a peptoid or peptoids that, when used as a vaccine, should provide broad protection against disease. This is particularly important for pathogens such as viruses that can evolve to evade the immune responses of their hosts. The use of MAbs is important because they recognize only the key protective epitope that will induce broadly neutralizing antibodies in an immunized vertebrate. By isolating peptoids that mimic highly conserved natural structures it is possible to generate broadly effective vaccines for whole classes of pathogens such that they will be less subject to immune evasion.

The steps of the method are generally as follows:

First, provide a selecting MAb that can inhibit or attenuate an entity that can cause a disease or abnormality, or neutralize a toxin; In the case of a pathogen, this MAb should ideally react with a broadly expressed highly conserved natural structure on all variants of that pathogen.

Second, provide a peptoid library that may or may not be tailored for use with the selecting MAb;

Third, eliminate from the peptoid library those peptoids that bind to antibodies of the same Ig class and from the same species as the said selecting antibody, and the anti-antibody ligand used to isolate the peptoid-antibody. i.e., to eliminate those peptoids that bind to portions of the antibody outside of the antigen combining region and are usually present on the Fc or the hinge region of the antibody; and to eliminate peptoids that bind to the secondary screening-retrieval ligands.

Fourth, add the selecting antibody to the remaining peptoids of the library to select peptoids that bind to the antigen-combining site of the said selecting antibody;

Fifth, select the antibody-bound peptoids away from peptoids not bound by said selecting antibody using a ligand for the selecting antibody and a retrieval system;

Sixth, in some cases, use a secondary screening system to confirm the specificity of the positively-selected peptoids obtained from Step 5. For example, this can be done by stripping the reagents from the selected beads and carrying out an on-bead colorimetric assay. In one example, the screening MAb can be added again. This would be followed by an enzyme-tagged secondary antibody and a substrate that would change color when it bound to the enzyme so that the colored beads could be visualized. Non-colored beads would be considered to represent false positives from the primary screening assay. In other cases only the secondary enzyme-tagged antibody and substrate would be added.

Additional screening steps may also be utilized.

In one embodiment, an on-bead library of peptoids or related mimics is incubated with a diluted or standardized buffer. First the library is screened with an irrelevant MAb and a retrieval system to eliminate peptoids that bind to other sites on the antibody. The remaining beads are then incubated with a MAb that recognizes a known or useful epitope, i.e., a protective antibody. The library is washed to remove the excess antibody. The peptoid bead-antibody complexes as well as free peptoids are further incubated with magnetic beads conjugated to a secondary antibody-binding ligand (either specific antibody directed against the monoclonal antibody, Protein A or Protein G, as appropriate).

Next, peptoids bound to the MAb and the magnetic bead are then isolated using a magnet. Isolated beads can then be stripped of all bound reagents and retested using an on bead ELISA to eliminate any false positives. Peptoids that remain positive can then be manually or instrument-selected by virtue of a color change in the ELISA, cleaved from the bead, sequenced using tandem MS, and synthesized in large quantity.

Finally, these scaled up peptoids can be tested in an ELISA to confirm they bind specifically to the screening MAb, and not to a species and isotype matched control IgG. If the ligand (pathogen, recombinant protein, prion, transfected cell, etc.) against which the original antibody was raised, is available, it can also be used to determine whether the peptoid and/or peptoid/peptide hybrid (alone or attached to a protein or nanoparticle) can block the binding of the MAb to it natural ligand.

A. Library Screening

Using on-bead libraries of millions of compounds, one can carry out selection using a MAb that is known to bind to a broadly conserved structure on, for example, a virus or group of viruses and neutralizes them. In this case, one would incubate the bead-displayed library with an irrelevant MAb of the same species and isotype followed by a an anti-Ig ligand-retrieval system in order to eliminate any beads that capture irrelevant IgG antibodies or bind to reagents in the retrieval system. The remaining beads would then be screened with the relevant MAb. The selected peptoid "hits" can be further validated by on-bead ELISAs. The hits that appear most promising from this screen can be cleaved from the bead using proline-aspartic acid-cysteine linker or methionine linker technology, sequenced and synthesized. First, the hits are tested in maleimide-activated plates using an ELISA. The positive peptoids hits are then attached in a multivalent array to a carrier protein and used in ELISAs to demonstrate that the hit(s) will preserve the binding activity to the MAb used for screening following conjugation to a carrier protein. When a molecule containing the native B cell epitope is known, competition assays using the peptoid alone or peptoid-protein conjugate to block the binding of the screening MAb to the natural B cell epitope on the toxin/pathogen/prion can be used. Following this validation, these peptoid-carriers can be used to immunize mice. In most cases immunizations will contain 1-50 μg of peptoid-carrier adsorbed to an adjuvant that can contain one or more immunostimulatory agents. Following the initial vaccination, and in a typical situation, two booster shots are given 1-2 months and 5-8 months later. Additional boosters can also be given. Seven-10 days after the last boost, blood is collected and serum prepared by standard techniques. These sera are tested by ELISA for the presence of anti-peptoid antibodies Animals can also be boosted again if antibody titers are low. A portion of the anti-peptoid antibodies should cross-react with the native structure on the pathogen or toxin. This can be directly tested in a binding assay. When they do bind they can be further evaluated for their ability to neutralize the pathogen, toxin or disease-causing entiry both in vitro and in vivo. Those peptoids (on the same or different carrier) that elicited this immune response constitute vaccine candidates and can then be used to immunize mice and other vertebrates such that protective antibodies actively are elicited prior to exposure to the infectious or toxic agent.

To develop efficient screening parameters for selecting mimetic vaccine peptoids, the inventor and colleagues initially used on-bead FLAG peptide as a B cell epitope to which a monoclonal anti-FLAG antibody can bind, as well as an on-bead "knockout" FLAG peptide, in which one amino acid has been substituted by alanine such that anti-FLAG antibody does not bind to its ligand (Slootstra et al., 1996). This provides a known antibody/antigen pair to develop screening methodology and apply these optimized parameters to screening more diverse peptoid libraries. To test the efficiency of the selection method, FLAG$^+$ beads were spiked into FLAG$^-$ peptide beads and/or a random sample from an on-bead peptoid library. The anti-FLAG MAb was then added and beads were washed to remove unbound antibody. PGDs were then added to the peptide or peptoid bead-antibody conjugates. PGDs are iron oxide-containing particles conjugated to protein G. After allowing binding of PGDs to antibody-bound peptide still containing non-binding peptoid or peptide beads, the complexes of peptide or peptoid bead-antibody-PGD were then captured and isolated with a magnet. Every step of this procedure has been optimized, and the isolation of "spiked" FLAG peptide beads was achieved at a >90% success rate (Table 2).

B. Testing Hits

Figure 2A:
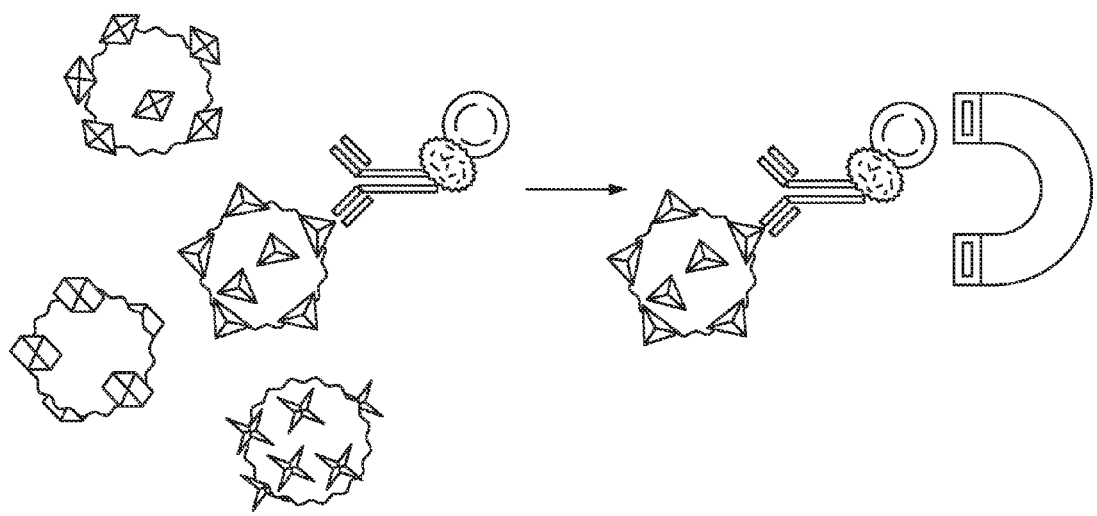
FIGS. 2A-B. Magnetic and color-based on-bead screening assays.
Figure 2B:
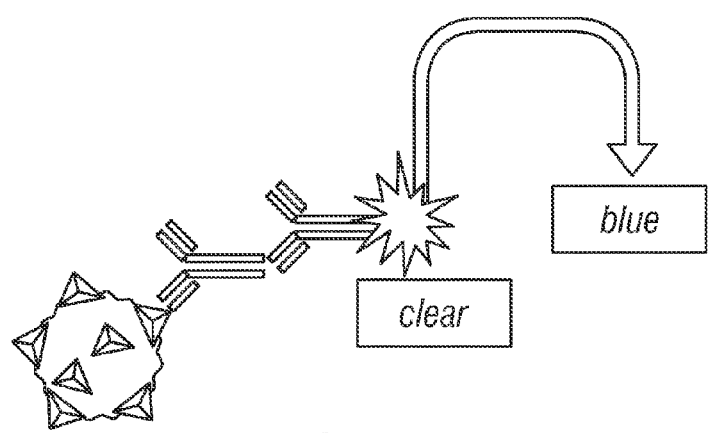

It is unlikely that every peptoid or related compound selected from a random library of several thousand to millions of molecules will be a "perfect" mimic for the native antigen of interest. For example, it might bind to the screening antibody with lower affinity. It might also be a false positive retrieved by the ligand-retrieval system. Several methods can be employed to validate peptoid hits and verify hits as vaccine candidates. First, the inventors have utilized an on-bead ELISA assay to confirm that they are binding the screening antibody (FIG. 2). This involves stripping the screening reagents from the beads, adding selecting antibody and an enzyme linked anti-antibody, the substrate for an enzyme that produces a color. The positive beads turn blue and can be isolated based on color. This quick test may eliminate the need for time consuming and expensive cleavage of all the originally isolated hits, high performance liquid chromatography (HPLC) purification, lyophilization, and conjugations to carrier proteins prior to retesting, since only peptoids that were positive in the ELISA would be developed further. Once the hits are validated by the on-bead ELISA, they are cleaved from the bead, sequenced, scaled up, and retested for binding to the antibody used to select them. It has been demonstrated that after a bead is used in this on bead ELISA, FLAG peptide itself or selected FLAG mimetic peptides can still be cleaved and sequenced to facilitate scale-up for further testing.

A robust, automated, high-throughput on-bead antibody binding assay for screening peptoid libraries against neutralizing MAbs can also be utilized. This involves using an automated workflow that combines magnetic bead isolation, fluorescence activated particle sorting using a Complex Object Parametric Analyzer and Sorter (COPAS) bead-sorting instrument, and quantitative confocal fluorescence imaging methods that enable the screening of large libraries on multiple antibody targets in a reasonable time. In order to discriminate true hits from false positive hits, the inventors can also employ high-throughput fluorescent polarization and fluorescence correlation spectroscopy (FCS) microvolume homogeneous binding assays that will be performed on cleaved peptoids from a single bead using laser scanning confocal microscopy system. The quantitative data from these solution-phase assays are used to rank library "hits" without the need for time and labor-consuming re-synthesis prior to hit identification. Once these true hits have been identified they can be sequenced by partial Edman degradation MS, MS/MS or electrospray mass spectrometry using electron-transfer dissociation (ETD) and collision induced dissociation (CID) fragmentation methods. The best hits identified by screening and sequencing.

The COPAS instrument is a fluorescence-activated particle sorter that unlike traditional fluorescence activated cell sorter (FACS) instrumentation is specifically designed to accurately analyze and sort particles from 20 to 1,500 microns in size. This instrument can be used to analyze and array the 90-500 micron beads from one-bead one-compound peptoid libraries that show sufficient binding fluorescence into 96-well plates. The COPAS instrument can sort beads at a rate of 100,000 beads an hour and has been shown to be effective for the on-bead screening and sorting of combinatorial libraries. Proteins can be removed from the so they can be used in secondary screening. Peptoids on the interior of the bead cab be reserved for sequencing.

C. Optimization of Hits

If the above experiments show that the peptoid or related compound hits from the screening experiment do not induce a sufficiently robust protective antibody response following their attachment to carrier and use as a vaccine, one in the art would hypothesize that these compounds are insufficient to provide good mimics of the unknown native epitope and that the anti-peptoid antibodies have insufficient affinity for that epitope to be protective. These peptoids can then be altered by glycine, sarcosine, or alanine scanning and evaluated for improved binding affinity for the screening antibody.

In this case, one would treat the peptoid or related compound hits as lead molecules and employ the techniques of medicinal chemistry to improve them. In the case where a native antigen is unknown, the goal will simply be to optimize the affinity of the peptoids selected for the selecting antibody. Peptoids or related compounds identified by such a procedure as having an improved affinity for the antibodies of interest would then be conjugated to carrier protein, adsorbed to alum and used to vaccinate animals and the biological testing described above would be repeated. This optimization protocol would be performed recursively as many times as necessary until a peptoid or related compound that is a sufficiently good mimic of the native antigen is found, as defined by the ability to bind the antibodies of interest with very high affinity and, more importantly, the ability to serve as the key element in a protective vaccine.

D. Peptoid Optimization

Much the same approach as described above can be used to further optimize the peptoids. A glycine, sarcosine or alanine scan can serve to identify the important side chains which could then be conservatively randomized. In this case, however, the newly created derivative libraries will be tested directly for competition with the native molecule. The goal in these experiments would be to identify peptoids or related compounds that have apparent binding constants, as determined in these competition binding experiments, closer to that of the native antigen. These would presumably be better three-dimensional mimics of the antigen which could then be tested using an in vivo vaccination/protection assay.

V. Vaccine Components

In other embodiments of the invention, the peptoid-carrier compositions used for vaccines may comprise additional immunostimulatory agents Immunostimulatory agents include but are not limited to an additional antigenic composition, an immunomodulator, an APC, an adjuvant or a carrier. In certain embodiments, the one or more additional agent(s) is covalently bonded to the antigen or an immunostimulatory agent, in any combination. Other immunopotentiating compounds are also contemplated for use with the compositions of the invention such as polysaccharides, including chitosan, which is described in U.S. Pat. No. 5,980,912, hereby incorporated by reference. Multiple (more than one) peptoids may be cross-linked to one another (e.g., polymerized). The use of small peptides for antibody generation or vaccination also typically requires conjugation of the peptide to an immunogenic carrier protein.

One of ordinary skill would know various assays to determine whether an immune response against a pathogen, toxin, prion or tumor-associated peptide was generated. The phrase "immune response" includes both cellular and humoral immune responses. Various B lymphocyte-antibody-based assays are well known, such as ELISAs, proliferation assays using peripheral blood lymphocytes (PBL), cytokine production and antibody production assays. See Benjamini et al. (1991), hereby incorporated by reference.

A. Adjuvants

As also well known in the art, the immunogenicity of a particular immunogen composition can be enhanced by the use of "non-specific" stimulators of the immune response, known as adjuvants. These adjuvants generally ramp up the innate immune response, which in turn makes the adaptive immune response more robust. They can also create depots at the site of vaccination so that the immunogen leaks into the body for a prolonged time. Adjuvants have been used experimentally to promote a generalized increase in immunity against poorly immunogenic antigens (e.g., U.S. Pat. No. 4,877,611). Immunization protocols have used adjuvants to stimulate responses for many years, and as such adjuvants are well known to one of ordinary skill in the art. Some adjuvants affect the way in which antigens are presented. For example, the immune response is increased when protein antigens are adsorbed to alum. Emulsification of antigens also prolongs the duration of antigen presentation and initiates an innate immune response. Suitable molecule adjuvants include all acceptable immunostimulatory compounds, such as cytokines, toxins or synthetic compositions.

Although Alum is an approved adjuvant for humans, adjuvants in experimental animals include complete Freund's adjuvant (a non-specific stimulator of the immune response containing killed *Mycobacterium tuberculosis*), incomplete Freund's adjuvants and aluminum hydroxide adjuvant. Other adjuvants that may also be used in animals and sometimes humans include interleukin (IL)-1, IL-2, IL-4, IL-7, IL-12, interferons, *Bacillus*-Calmette-Guérin (BCG), aluminum hydroxide, muramyl dipeptide (MDP) compounds, such as thur-MDP and nor-MDP (N-acetylmuramyl-L-alanyl-D-isoglutamine MDP), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. Major Histocompatibility Complex (MHC) antigens may even be used.

In one aspect, and approved for humans, an adjuvant effect is achieved by use of an agent, such as alum, used in about 0.05 to about 0.1% solution in phosphate buffered saline. Alternatively, in experimental animals the antigen is made as an admixture with synthetic polymers of sugars (Carbopol®) used as an about 0.25% solution. Adjuvant effects may also be achieved by aggregation of the antigen in the vaccine by heat treatment with temperatures ranging between about 70° to about 101° C. for 30 seconds to 2-minute period, respectively. Aggregation by reactivating with pepsin treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is MDP, a bacterial peptidoglycan. The effects of MDP, as with most adjuvants, are not fully understood, although the inventor is now beginning to understand that they activate cells of the innate immune system, i.e., dendritic cells, macrophages, neutrophils, NKT cells, NK cells, etc. MDP stimulates macrophages but also appears to stimulate B cells directly. The effects of adjuvants, therefore, are not antigen-specific. If they are administered together with a purified antigen, however, they can be used to selectively promote the response to the antigen.

In certain embodiments, hemocyanins and hemoerythrins may also be used in the invention. The use of KLH is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative muramyl tripeptide phosphatidylethanolamide (MTPPE) are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. This is effective in activating human monocytes and destroying tumor cells, but is non-toxic in generally high doses. The compounds of U.S. Pat. No. 4,950,645 and PCT Patent Application WO 91/16347 are contemplated for use with cellular carriers and other embodiments of the present invention.

BCG and BCG-CWS may also be used as adjuvants, with or without TDM. TDM may be used itself. TDM administration has been shown to correlate with augmented resistance to influenza virus infection in mice (Azuma et al., 1988). TDM may be prepared as described in U.S. Pat. No. 4,579,945. BCG is an important clinical tool because of its immunostimulatory properties. BCG acts to stimulate the reticuloendothelial system (RES), activates natural killer (NK) cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE BCG (Organon Inc., West Orange, N.J.).

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present invention.

Another group of adjuvants are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with TDM is particularly contemplated, as described in U.S. Pat. No. 4,435,386. Combinations of detoxified endotoxins with TDM and endotoxic glycolipids is also contemplated (U.S. Pat. No. 4,505,899), as is combination of detoxified endotoxins with CWS or CWS and TDM as described in U.S. Pat. Nos. 4,436,727, 4,436,728 and 4,505,900. Combinations of just CWS and TDM, without detoxified endotoxins, are also envisioned to be useful, as described in U.S. Pat. No. 4,520,019.

Those of skill in the art will know the different kinds of adjuvants that can be conjugated to or adsorbed to vaccines in accordance with this invention and which are approved for human vs. experimental use. These include alkyl lysophosphilipids (ALP), BCG, and biotin (including biotinylated derivatives) among others. Certain adjuvants particularly contemplated for use are the teichoic acids from Gram⁻ bacterial cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Various adjuvants, even those that are not commonly used in humans, may still be employed in animals. Adjuvants may be encoded by a nucleic acid (e.g., DNA or RNA). It is contemplated that such adjuvants may be also be encoded in a nucleic acid (e.g., an expression vector) encoding the antigen, or in a separate vector or other construct. Nucleic acids encoding the adjuvants can be delivered directly, such as for example with lipids or liposomes.

B. Biological Response Modifiers (BRMs)

In addition to adjuvants, it may be desirable to co-administer BRMs, which have been shown to up-regulate T cell immunity or down-regulate suppressor cell activity. Such BRMs include, but are not limited to: cimetidine (CIM; 1200 mg/d) (SmithKline Beecham, Pa.); low-dose cyclophosphamide (CYP; 300 mg/m$^2$) (Mead Johnson & Co., NJ), cytokines such as gamma-interferon, IL-2, or IL-12 or genes encoding proteins involved in immune helper functions, such as the B7 (CD87) costimulatory molecule.

C. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-α, MIP1-β, IP-10 and combinations thereof. The skilled artisan will recognize that certain cytokines are also known to have chemoattractant effects and could also be classified under the term chemokines.

D. Immunogenic Carrier Proteins

In certain embodiments, an antigenic composition may be chemically coupled to a carrier or recombinantly expressed with an immunogenic carrier peptide or polypeptide (e.g., an antigen-carrier fusion peptide or polypeptide) to enhance an immune reaction. Exemplary and preferred immunogenic carrier amino acid sequences include hepatitis B surface antigen (HBsAg), tetanus toxoid, reduced diphtheria toxoid, keyhole limpet hemocyanin (KLH) and bovine serum albumin (BSA). In humans tetanus toxoid would be advantageous since it is already an approved protein vaccine. For experimental animals, other albumins such as ovalbumin (OVA), mouse serum albumin or rabbit serum albumin also can be used as immunogenic carrier proteins. Means for conjugating a polypeptide or peptide to an immunogenic carrier protein are well known in the art and include, for example, glutaraldehyde, m-maleimidobenzoyl-N-hydroxysuccinimide ester, carbodiimide and bis-biazotized benzidine. It should be noted that many different peptoids for the same or different pathogens/toxins/prions could be attached to a carrier molecule such as tetanus toxoid to vaccinate against multiple pathogens/toxins/prions with 1-3 vaccinations of tetanus toxoid.

VI. Immunotherapy

In an embodiment of the present invention, methods of treatment and prevention of disease are contemplated. An effective treatment, generally, is defined as sufficient to detectably and repeatedly to ameliorate, reduce, minimize or limit the extent of the disease or condition or symptoms thereof. More rigorous definition may apply, including elimination, eradication or cure of disease.

A. Active Immunization

In one particular aspect, the invention addresses the induction of an immune response in a naïve subject, i.e., active immunity. The routes of administration will vary, depending upon the location and nature of the disease, and include, e.g., intradermal, transdermal, intramuscular, intranasal, subcutaneous, percutaneous and oral administration and formulation. All that is required is that an immunogenic form of the antigen be presented to the appropriate immune cells such that a robust and protective immune response can be generated.

Vaccinations may be repeated as necessary to generate a sufficient immune response. The generation of protective antibodies may be determined using techniques known to those of skill in the art. Where a protective immune response has been generated, but sufficient time has lapsed such that the response is no longer sufficiently robust to be protective, a "booster" vaccine may be employed.

B. Adoptive Immunotherapy

In adoptive immunotherapy, the patient's circulating lymphocytes are isolated in vitro, activated by lymphokines such as IL-2 or transduced with genes for tumor necrosis factor, and re-administered (Rosenberg et al., 1988; 1989). To achieve this, one would administer to an animal, or human patient, an immunologically effective amount of activated lymphocytes in combination with an adjuvant- or carrier-incorporated peptoid composition as described herein. The activated lymphocytes will most preferably be the patient's own cells that were earlier isolated from a blood or tumor sample and activated (or "expanded") in vitro.

C. Passive Immunotherapy

A number of different approaches for passive immunotherapy exist. They may be broadly categorized into the following: injection of antibodies alone; or the injection of antibodies coupled to other agents. Preferably, human MAbs are employed in passive immunotherapy, as they produce few or no side effects in the patient. It may be favorable to administer more than one MAb directed against several different antigens or epitopes or even antibodies with multiple antigen specificity. Treatment protocols also may include administration of lymphokines or other immune enhancers as described by Bajorin et al. (1988).

D. Injectable Compositions and Formulations

One method for the delivery of a pharmaceutical according to the present invention is systemically. However, depending upon the context, the pharmaceutical compositions disclosed herein may alternatively be administered parenterally, intravenously, subcutaneously, intradermally, intramuscularly, transdermally or even intraperitoneally as described in U.S. Pat. Nos. 5,543,158; 5,641,515 and 5,399,363 (each specifically incorporated herein by reference in its entirety).

Injection may be by syringe or any other method used for injection of a solution, as long as the agent can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery. Intradermal or transdermal administration of a vaccine is also possible and could involve the use of small needles or patches.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy and safe administration by a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermolysis fluid or injected at the proposed site of infusion, (see for example, "Remington's Pharmaceutical Sciences," $15^{th}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "buffer or diluent" includes any and all solvents, dispersion media, vehicles, coatings, diluents, excipients, antibacterial and antifungal agents, isotonic and absorption delaying agents, buffers, solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrases "pharmaceutically-acceptable" or "pharmacologically-acceptable" refer to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Proof of Principle Using Flag Peptides

As an initial proof of principle to show that specific MAb-binding peptides can be recovered from a library of irrelevant peptides, an anti-FLAG peptide MAb was used to screen a mixture of peptides that did or did not react with an anti-peptide MAb. Five FLAG$^+$ peptide beads were spiked into 250 μL FLAG$^-$ beads (approximately 30,000 beads). Each "spike" was performed in triplicate tubes. The mixture was screened as described using 10 μg/mL of a MAb mouse anti-FLAG and Protein G coupled magnetic Dynabeads (Invitrogen) (PGDs). Positive beads were isolated using a magnet. Beads retained by the MAb/PGDs on the magnet were counted, washed in 50% acetonitrile (ACN)/H$_2$O and distributed at one bead per tube. These beads were then cleaved with cleavage cocktail, sequenced using MALDI MS and MS/MS (TABLE 2) and chemical compounds composed of structures conserved between hit compounds were synthesized. As shown the positive beads could be recovered from the mixture of positive and negative beads using this technology.

EXAMPLE 2

Peptoids are Immunogenic when Conjugated to a Protein Carrier

Figure 3A:
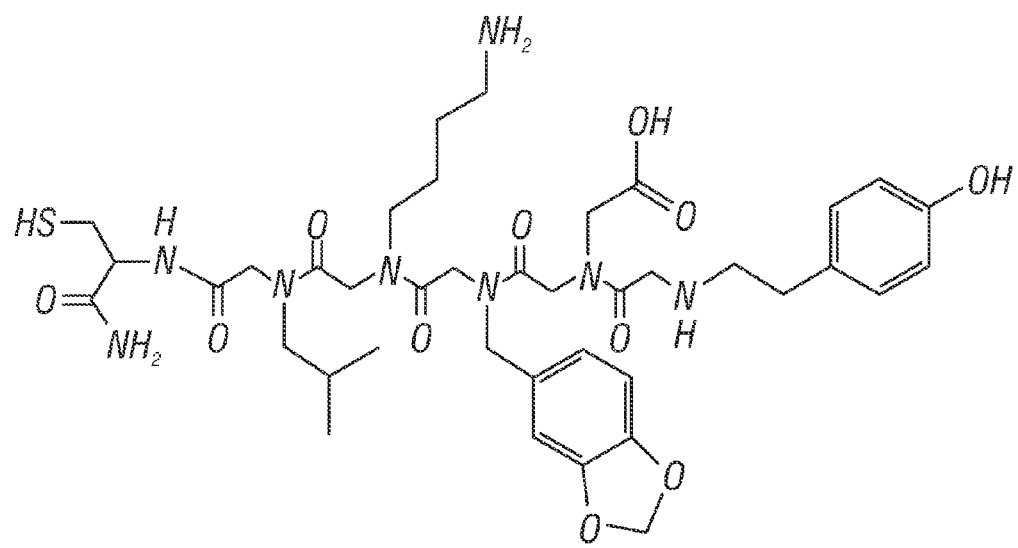
FIGS. 3A-B. Schematic representation of the chemical structures of the R5A peptoid (FIG. 3A) and the irrelevant control RC peptoid (FIG. 3B). A cysteine (Cys) residue was first added to allow eventual conjugation of the compound to maleimide-activated carrier proteins or coupling to Sulfo-Link® resin. This Cys residue also provided a known mass for ease of sequencing by matrix-assisted laser desorption/ionization (MALDI) time-of-flight/time-of-flight (TOF/TOF) tandem mass spectrometry (MS/MS).
Figure 4A:
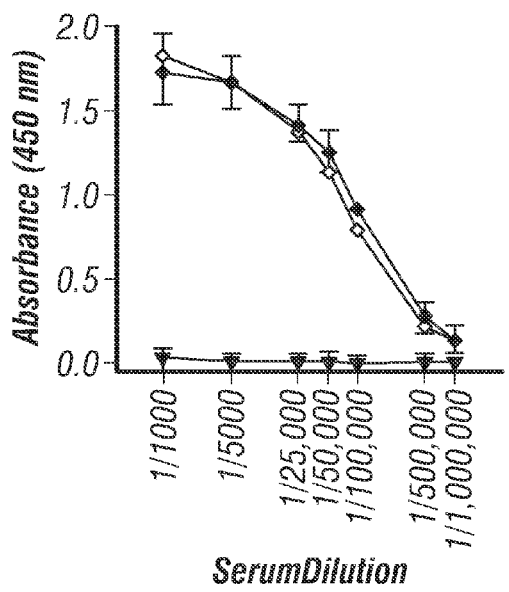
FIGS. 4A-D. Purification of rabbit anti-R5A peptoid (RAR5A) polyclonal antibodies (PAbs) from the serum of a rabbit named "12D". This rabbit was immunized with R5A conjugated to KLH via maleimide chemistry (R5A-m-KLH) and adsorbed to alum.
Figure 4B:
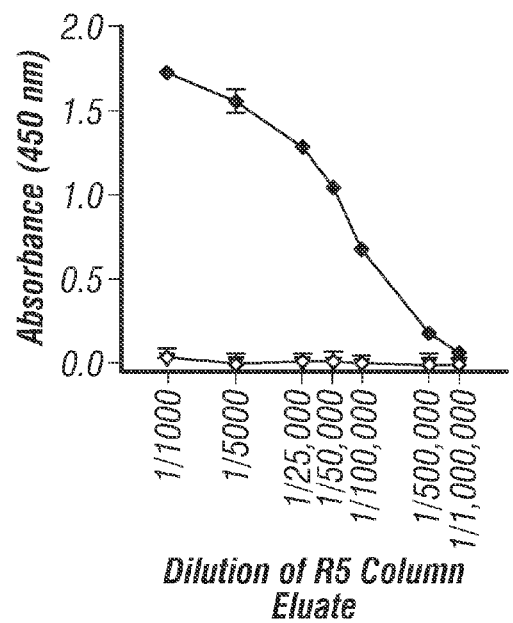
Figure 4C:
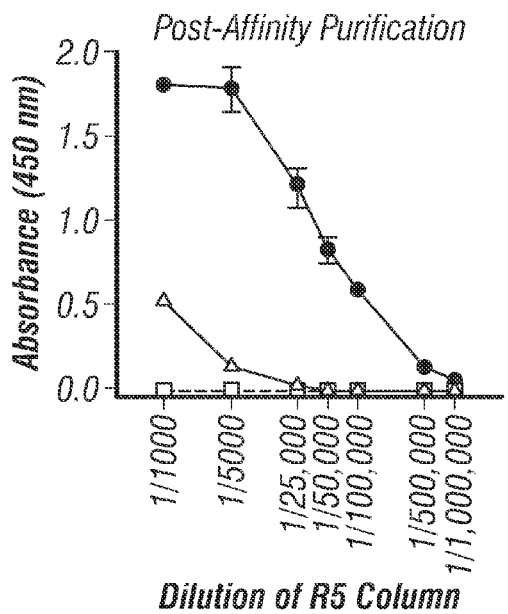
Figure 4D:
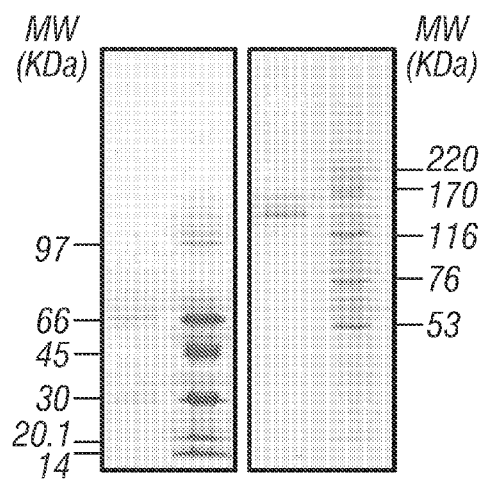

To generate and affinity purify anti-peptoid PAbs, a five monomer peptoid, R5A, was designed (FIG. 3A) and conjugated to a carrier protein, KLH, and used to immunized two rabbits. The rabbits were bled before immunization (pre-bleed) and following immunizations. As determined by ELISA, no antibody against any component of the peptoid conjugate was present in pre-immunization serum (FIGS. 4A-C). Antibody titers were detected post-immunization against each of the three components of the immunizing peptoid conjugate, the peptoid, the carrier and the linker (FIG. 4A). To purify RAR5A PAb, R5A-Sepharose affinity chromatography was performed, and subsequent ELISAs demonstrated the removal of anti-linker and anti-carrier antibodies (FIGS. 4B-C). The structural integrity of RAR5A was confirmed by SDS-PAGE (FIG. 4D). These experiments demonstrated that specific anti-peptoid antibodies can be generated and purified using the methods described in the written description of the patent.

EXAMPLE 3

Proof of Principle of Peptoid Library Screening Using the R5A Peptoid

Figure 3B:
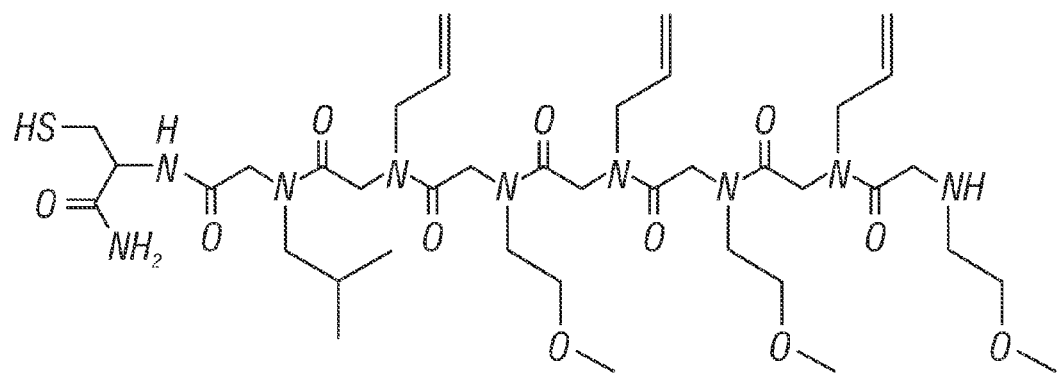

The affinity purified anti-R5A peptoid antibodies (RAR5A) were used to screen a mixture of specific and irrelevant peptoids. First, an irrelevant peptoid named RC was designed and synthesized (FIG. 3B). After, small-scale experiments were first conducted in which tubes containing three R5A peptoid beads spiked into 27 irrelevant RC peptoid beads were prepared, and to which a series of concentrations of RAR5A were then added. The results presented in the TABLE 3 indicated that RAR5A bound specifically to R5A peptoid in this on-bead assay.

For the further optimization of magnetic screening assay, the inventor used a constant concentration of screening antibody, 1 μg/mL RAR5A along, with a series of PGD dilutions at the 500 μL volume. As shown in TABLE 4, a PGD solution as dilute as 1:5,000 could retain 100% of the spiked R5A peptoid beads across three similar experiments. It was concluded that when antibody concentration against an on-bead ligand is high enough, the PGD binding threshold for retention of that on-bead ligand by the magnet is quite low compared with the dilution of PGDs that had been used based on the peptide-optimized screening experiments, from which higher concentrations of antibody and PGDs were adopted than appeared saturating so as not to miss any on-bead peptoids of interest in magnetic screening.

These small-scale experiments also provided a starting point for larger, screening-scale experiments using tubes containing three R5A peptoid beads spiked into approximately 20,000 RC peptoid beads or 20,000 beads from a peptoid library (named 1) (TABLE 5). Increasing concentrations of RAR5A were added in each round of screening until the three R5A peptoid beads were retained (TABLE 5). The screening conditions determined in the above preliminary experiments were used to screen peptoid libraries with neutralizing MAbs targeting ricin toxin, and pathogens (HIV, murine norovirus type (1 MNV-1)).

EXAMPLE 4

Antibody Selection of Peptoid Mimetics for a Toxin or for Several Pathogens

On-bead peptoid libraries were screened with the antibodies referenced in the footnotes to TABLES 6-8. These MAbs are neutralizing for the two pathogens or the one toxin in question. TABLES 6-8, column 2 shows the number of peptoid sequenced identified by the selecting antibody using magnetic screening; column 3 is the number of peptoid sequences that were further selected by the on-bead ELISA (color screening); column 4 lists the diversity of the number of on-bead compounds screened to retain these potential B cell epitope mimetics. After cleaving the peptoid off of its TentaGel support sequences were determined by MALDI MS and MS/MS.

EXAMPLE 5

An Anti-Peptoid Hit Recovered with a MAb Against a Ricin Epitope is Specific Specific ricin mimetics were identified when the peptoid libraries were screened with MAbs against known linear epitopes of ricin A chain (GD12 MAb which binds a linear epitope in the native protein from T16 to M174; R70 MAb which binds a linear epitope from N97 to F108), as well as known a conformational epitope (RACA18 MAb). Peptoid hits for all the MAbs were identified (TABLE 6). These peptoids were sequenced, synthesized, conjugated to carrier proteins and then re-evaluated for their interaction with the corresponding screening MAb using ELISAs.

Figure 5A:
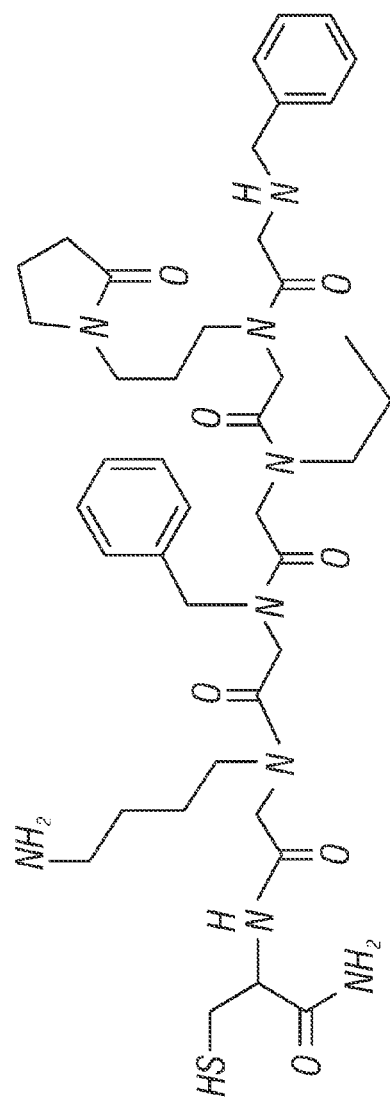
FIGS. 5A-B. Schematic representation of the chemical structures of the PGD12.4 (FIG. 5A) and the PGD12.4L (FIG. 5B) peptoids. A cysteine (Cys) residue was first added to allow eventual conjugation of the compound to maleimide-activated carrier proteins. This Cys residue also provided a known mass for ease of sequencing by MS/MS.
Figure 5B:
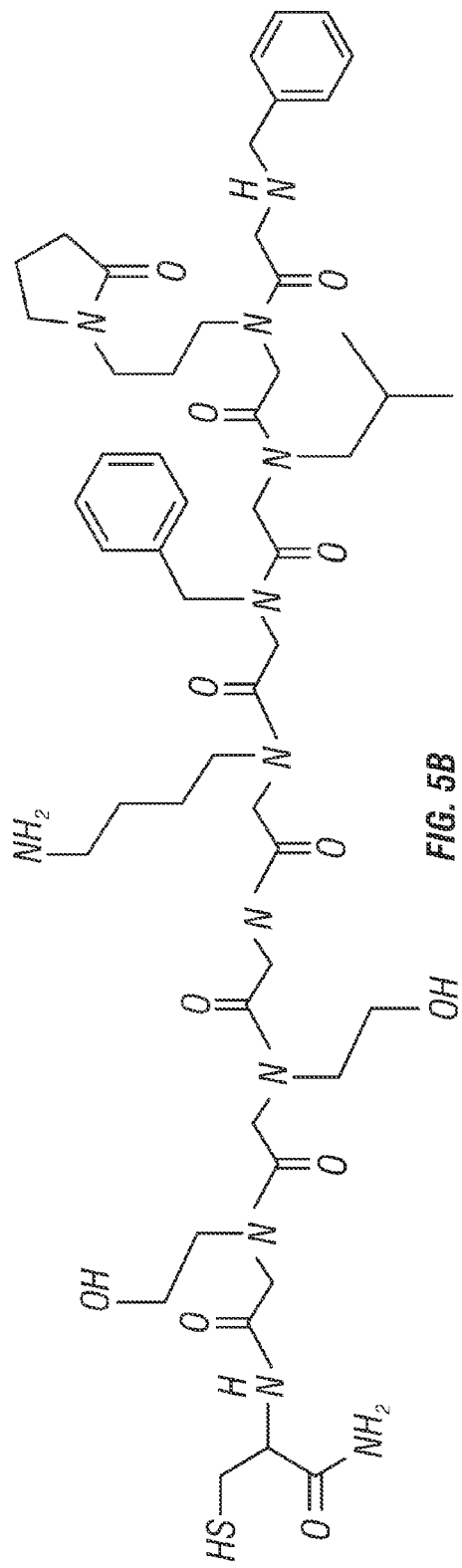
Figure 6:
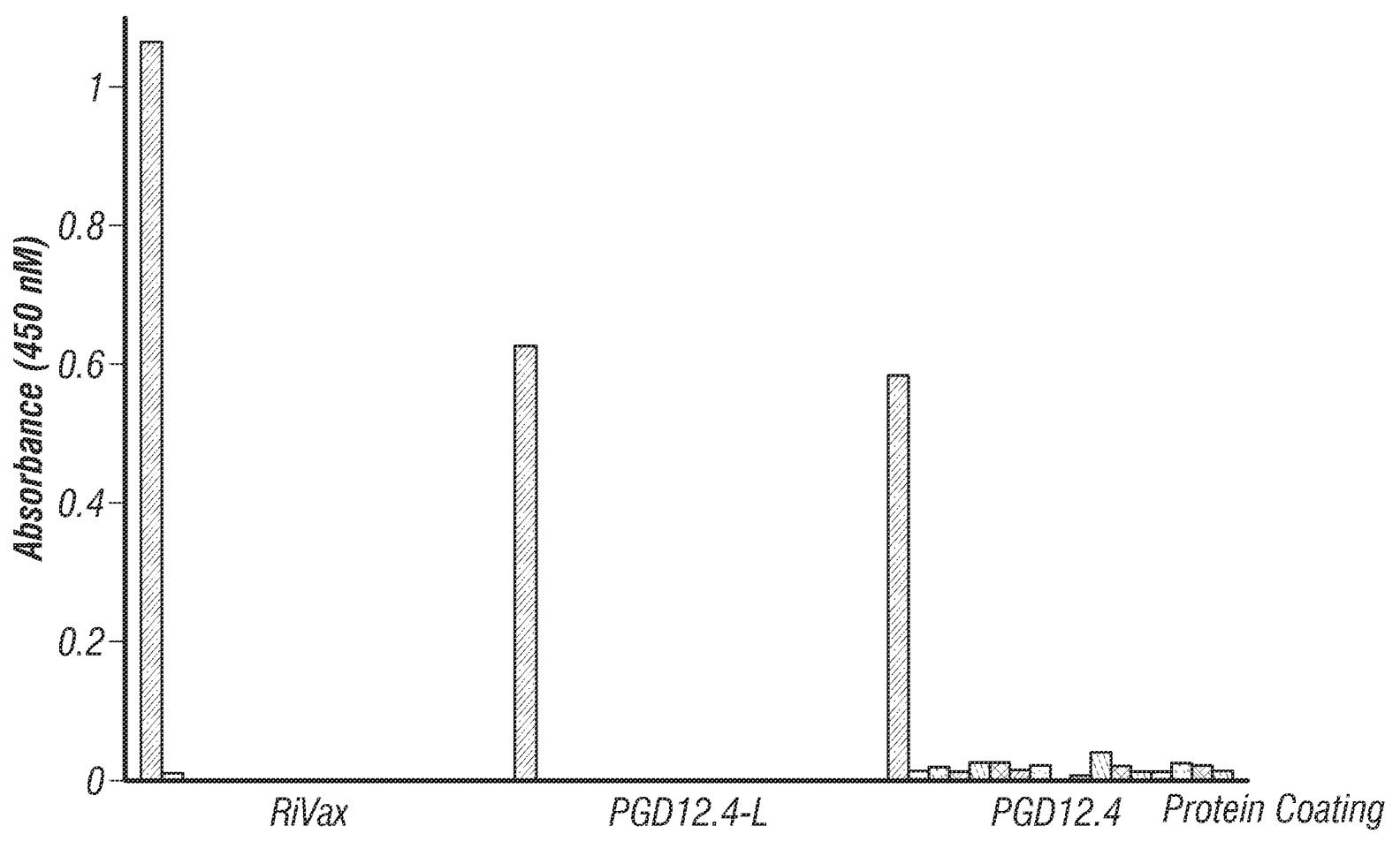
Figure 7A:
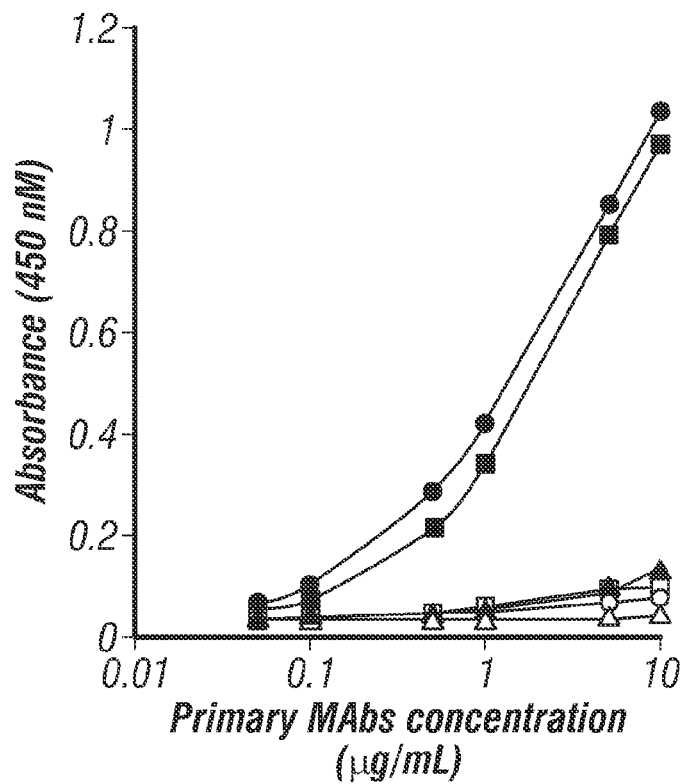
Figure 7B:
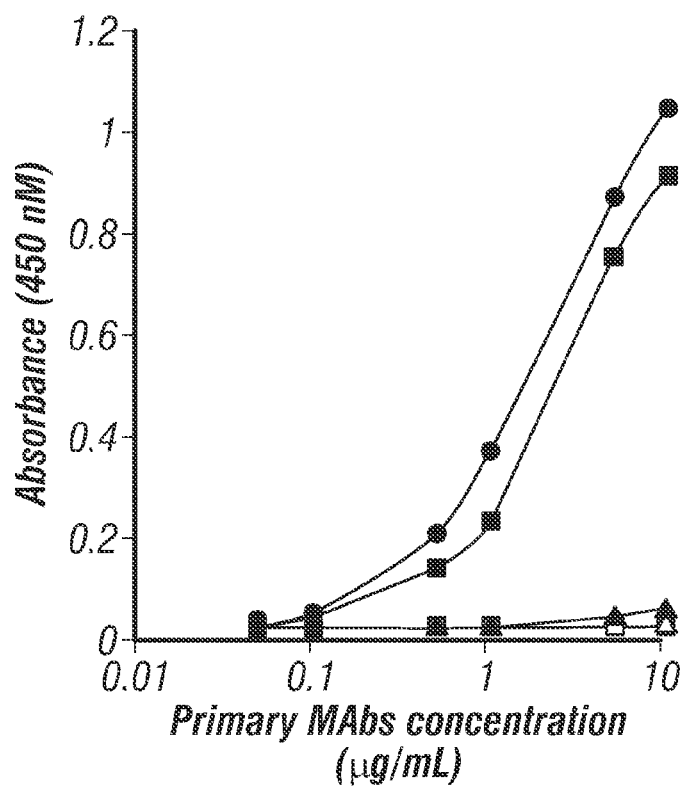
Figures 8A, 8B:
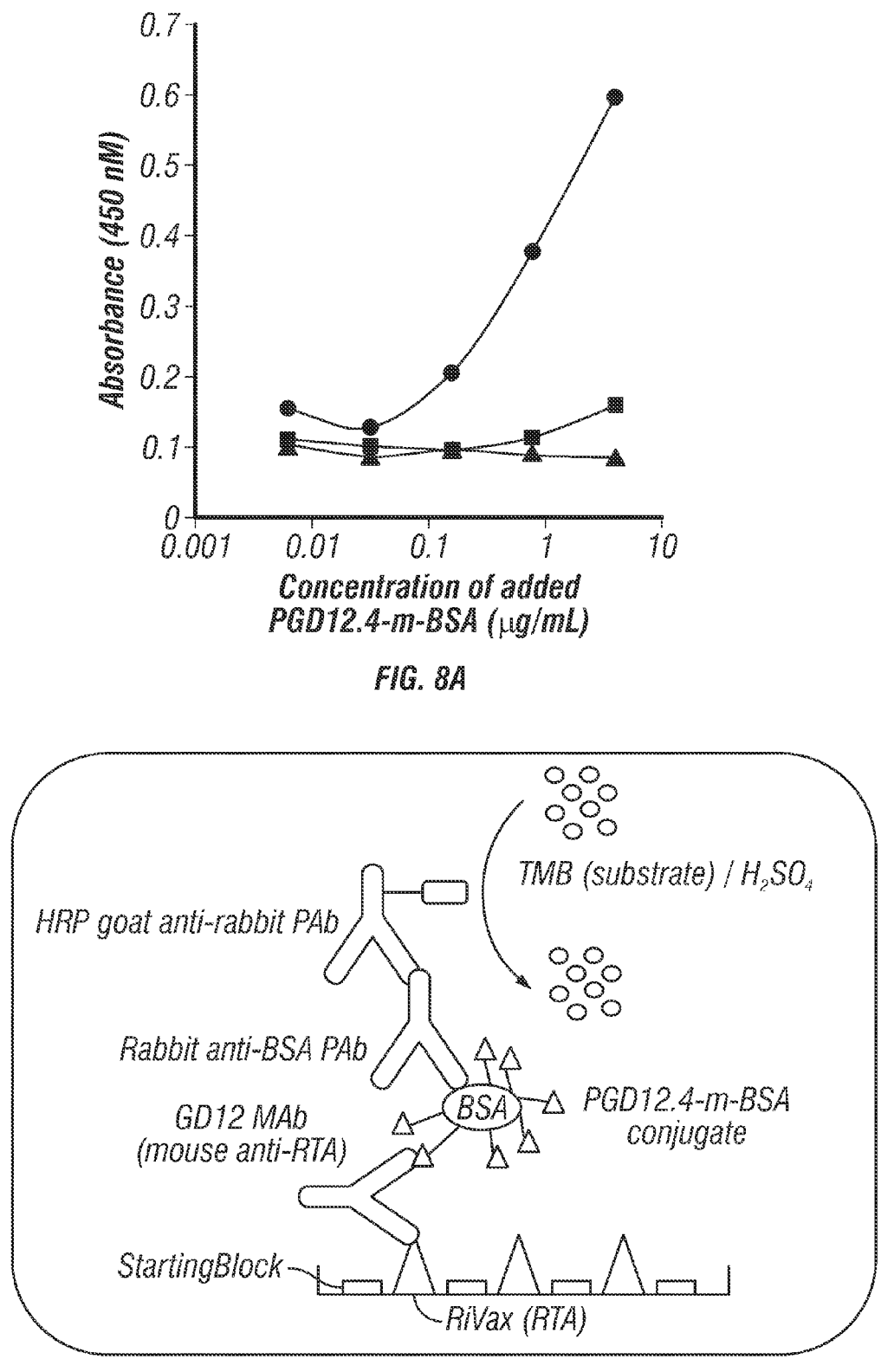

One of the mimetic candidates recognized by GD12.4 (named PGD12.4) is shown in FIG. 5A. The GD12 MAb recognized the positive control, RiVax, as well as the PGD12.4 peptoid coated onto a maleimide-activated ELISA plate (FIG. 6). It was not recognized by a panel of negative control isotype-matched MAbs. Moreover, the specificity of PGD12.4 was preserved following its conjugation to a carrier protein, BSA (FIGS. 7A and 8A). The inventors also attached the peptoid to the carrier using a "spacer" containing two molecules of ethanolamine between the cysteine and the peptoid, to prevent steric hindrance (named PGD12.4L) (FIG. 5B). This was also positive in the ELISA using maleimide-activated ELISA plates (FIG. 6). The activity of PGD12.4-L was also conserved following conjugation to BSA as shown by ELISA (FIG. 7B).

TABLE 3

RAR5A binds specifically and reproducibly to on-bead R5A-peptoid versus irrelevant RC-peptoid beads in small-scale magnetic screening assays

| RAR5A antibody concentration (μg/mL) | Number of TentaGel beads after magnetic screening[1] | | |
|---|---|---|---|
| | Retained | | |
| | Total (PGD coverage) | Confirmed as R5A by MS/MS | Not retained |
| 0 | 0 | 0 | 30 |
| 0.0001 | 0 | 0 | 30 |
| 0.001 | 0 | 0 | 30 |
| 0.01 | 0 | 0 | 30 |
| 0.1 | 1 (sparse) | 0 | 27 |
| 1 | 2 (sparse) | 2 | 27 |
| 10 | 3 (covered) | 3 | 27 |

[1] Three R5A peptoid beads were added to tubes of 27 RC peptoid beads to give a total of 30 beads in each tube. Data shown are from one representative experiment of three performed. In parallel, three R5A peptoid beads were added to tubes of twenty seven RC peptoid beads and screened with an irrelevant affinity purified rabbit anti mouse Ig (RAMIg), at the concentrations shown; no on-bead peptoids were retained by the magnet (data not shown).
[2] PGDs were added a 1:10 dilution (3 mg/mL) to peptoid beads that had been previously incubated with RAR5A.

TABLE 4

Diluted solutions of PGDs specifically and routinely select complexes of on-bead R5A peptoid and RAR5A from irrelevant RC peptoid beads in small-scale assays

| Dilution of PGD stock[2] | Number of TentaGel beads after magnetic screening[1] | | |
|---|---|---|---|
| | Retained | | |
| | Total (PGD coverage) | Confirmed as R5A by MS/MS | Not retained |
| 0 | 0 | — | 30 |
| 1:100000 | 0 | — | 30 |
| 1:50000 | 0 | — | 30 |
| 1:25000 | 0 | — | 28 |
| 1:10000 | 3 (hardly any) | 3 | 27 |
| 1:5000 | 3 (sparse) | 2 | 27 |
| 1:2500 | 3 (sparse) | 3 | 27 |
| 1:1000 | 3 (2 covered, 1 sparse) | 3 | 27 |
| 110 | 3 (covered) | 2 (1 bead lost) | 25 |

[1] Three R5A peptoid beads were added to tubes of 27 RC peptoid beads to give a total of 30 beads in each tube. Data shown are from one representative experiment of three performed.
[2] PGDs were added at a range of dilutions from 0 to 1:10 (0-3 mg/mL) to peptoid beads that had been previously incubated with 1 μg/mL RAR5A. In parallel, three R5A peptoid beads were added to tubes of twenty seven RC peptoid beads, then screened with an irrelevant antibody, RAMIg, at 1 μg/mL and the range of PGD dilutions shown; no on-bead peptoids were retained by the magnet (data not shown).

TABLE 2

The retention of on-bead FLAG+ peptide added to pools of irrelevant FLAG− peptide by magnetic screening is highly sensitive and specific

| | Number of: | | | |
|---|---|---|---|---|
| FLAG+ peptide beads added | Beads retained by magnetic screening | MS[1]-confirmed FLAG+ peptide beads retained by magnetic screening | MS-confirmed FLAG− peptide beads retained by magnetic screening[2] | Beads unreadable by MS |
| 5 | 14 | 5 | 9 | 0 |
| 5 | 7 | 5 | 2 | 0 |
| 5 | 5 | 5 | 0 | 0 |

[1] Mass spectrometry
[2] "Cracked" resin bound non-specific by protein G (Chen et al., 1996)

TABLE 5

Selection of R5A-peptoid beads by RAR5A from a mixture of many on-bead peptoids requires a higher concentration of RAR5A than selection of R5A-peptoid beads from many irrelevant RC-peptoid beads

| | | Number of TentaGel beads | | | | | |
|---|---|---|---|---|---|---|---|
| RAR5A antibody | | Added | | | Retained by magnetic screening[1] | | |
| | | | | | | Confirmed by MS[2] | |
| Round | concentration (μg/mL) | R5A | RC | Peptoid Library 1 | Total | R5A | RC | Peptoid Library 1 |
| 1 | 0 | | | | 0 | — | — | — |
| 2 | 0.01 | 3 | 20,000 | — | 0 | — | — | — |
| 3 | 0.1 | | | | 3 | 3 | — | — |
| 4 | 1 | | | | 0 | — | — | — |
| 1 | 0 | | | | 11 | 0 | — | 11 |
| 2 | 0.01 | 3 | — | 20,000 | 1 | 0 | — | 1 |
| 3 | 0.1 | | | | 2 | 0 | — | 2 |
| 4 | 1 | | | | 51 | 3 | — | 48 |

[1]Three TentaGel-R5A peptoid beads were added to tubes containing approximately 20,000 TentaGel beads bearing RC or peptoids from the Peptoid Library 1, and 4 rounds of magnetic screening were performed. In the first round, the beads were washed with PBST, and magnetic PGDs were added to a final dilution of 1:10, or 3 mg/mL in PBST. The tubes containing this mixture were incubated for 30 minutes on a rotisserie before being placed on a magnet. Those beads not retained by the magnet were removed by pipetting, washed with PBST, and incubated with RAR5A PAb at 0.01 μg/mL in PBST for one hour on a rotisserie to begin Round 2. Following washing with PBST, PGDs were applied and TentaGel beads not retained by the magnet were removed as in Round 1. The antibody concentration was then increase in Round 3 to 0.1 μg/mL and to 1 μg/mL in Round 4. For each round, the TentaGel beads retained by the magnet were counted using a light microscope at 40X power, and the peptoid sequence on each TentaGel bead retained was determined by separating the beads into individual tubes, cleaving the peptoid from the bead, and analyzing the cleaved peptoid by MALDI MS and MS/MS. In parallel, three TentaGel-R5A beads were added to approximately 20,000 RC beads and screened with an irrelevant rabbit PAb, RAMIg; no R5A Beads were retained by the magnet (data not shown). Data shown are from one representative experiment of three performed.
[2]If R5A or RC was suspected based on MS, MS/MS was performed.

TABLE 6

Potential ricin vaccine peptoid mimetics identified in 250 μL of peptoid library resin

| Screening neutralizing monoclonal antibody | Number of potential mimetic peptoids identified in magnetic screening | Number of potential mimetic peptoids identified in on-bead ELISA | Library diversity |
|---|---|---|---|
| A18[1] | 40 | 8 | $1 \times 10^5$ |
| GD12[2] | 259 | 7 | $1 \times 10^5$ |
| R70[3] | 11 | 8 | $1 \times 10^5$ |

[1]Maddaloni et al. (2004)
[2]Neal et al. (2010)
[3]Lemley et al. (1994)

TABLE 7

Potential murine norovirus type 1 (MNV-1) peptoid mimetics identified in 250 μL of peptoid library resin

| Screening neutralizing monoclonal antibody | Number of potential mimetic peptoids identified in magnetic screening | Number of potential mimetic peptoids identified in on-bead ELISA | Library diversity |
|---|---|---|---|
| A6.2[1-3] | 44 | 7 | $1 \times 10^5$ |

[1]Wobus et al. (2004)
[2]Chachu et al. (2008)
[3]Katpally et al. (2008)

TABLE 8

Potential HIV peptoid mimetics identified 250 μL of peptoid library resin

| Screening neutralizing monoclonal antibody | Number of potential mimetic peptoids identified in magnetic screening | Number of potential mimetic peptoids identified in on-bead ELISA | Library diversity[1] |
|---|---|---|---|
| PG9[2] | 21 | 0 | $1 \times 10^5$ |
| PG16[2] | 10 | 1 | $1 \times 10^5$ |
| PG9 | 4 | 4 | $16 \times 10^6$ |
| PG16 | 16 | 16 | $16 \times 10^6$ |
| PG9 | 13 | 14 | $1.4 \times 10^6$ |
| PG16 | 1 | 1 | $1.4 \times 10^6$ |

[1]Three independent peptoid libraries were investigated
[2]Walker et al. (2009)

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 4,196,265
U.S. Pat. No. 4,435,386
U.S. Pat. No. 4,436,727
U.S. Pat. No. 4,436,728
U.S. Pat. No. 4,505,899
U.S. Pat. No. 4,505,900
U.S. Pat. No. 4,520,019
U.S. Pat. No. 4,554,101
U.S. Pat. No. 4,579,945
U.S. Pat. No. 4,684,611
U.S. Pat. No. 4,797,368
U.S. Pat. No. 4,866,034
U.S. Pat. No. 4,877,611
U.S. Pat. No. 4,879,236
U.S. Pat. No. 4,950,645
U.S. Pat. No. 4,952,500
U.S. Pat. No. 5,139,941
U.S. Pat. No. 5,302,523
U.S. Pat. No. 5,322,783
U.S. Pat. No. 5,384,253
U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,609,870
U.S. Pat. No. 5,610,042
U.S. Pat. No. 5,641,515
U.S. Pat. No. 5,656,610
U.S. Pat. No. 5,693,762
U.S. Pat. No. 5,702,932
U.S. Pat. No. 5,736,524
U.S. Pat. No. 5,739,169
U.S. Pat. No. 5,780,448
U.S. Pat. No. 5,785,970
U.S. Pat. No. 5,789,215
U.S. Pat. No. 5,801,005
U.S. Pat. No. 5,824,311
U.S. Pat. No. 5,830,880
U.S. Pat. No. 5,846,225
U.S. Pat. No. 5,846,233
U.S. Pat. No. 5,846,945
U.S. Pat. No. 5,861,155
U.S. Pat. No. 5,871,986
U.S. Pat. No. 5,945,100
U.S. Pat. No. 5,980,912
U.S. Pat. No. 5,981,274
U.S. Pat. No. 5,994,136
U.S. Pat. No. 5,994,624
U.S. Pat. No. 6,013,516
U.S. Pat. No. 6,020,192
U.S. Pat. No. 6,027,727
U.S. Pat. No. 6,054,297
Aichele et al., *J. Exp. Med.*, 182:261-266, 1995.
Alam et al., *Nature*, 381:616-620, 1996.
Alexander-Miller et al., *J. Exp. Med.*, 184:485-492, 1996.
Alexander-Miller et al., *J. Exp. Med.*, 188:1391-1399, 1998.
Alexander-Miller et al., *Proc. Natl. Acad. Sci. USA*, 93:4102-4107, 1996.
Altman et al., *Science*, 274:94-96, 1996.
Anderton et al., *J. Exp. Med.*, 193:1-11, 2001.
Antin, *Blood*, 82:2273-2277, 1993.
Arap et al., *Cancer Res.*, 55(6):1351-1354, 1995.
Austin-Ward and Villaseca, *Rev. Med. Chil.*, 126(7):838-45, 1998.
Azuma et al., *Cell Immunol.*, 116(1):123-134, 1988.
Baichwal and Sugden, In: *Gene Transfer*, Kucherlapati (Ed.), NY, Plenum Press, 117-148, 1986.
Bajorin et al., *J. Clin. Oncol.*, 6(5):786-92, 1988.
Bakhshi et al., *Cell*, 41(3):899-906, 1985.
Ballieux et al., *Clin. Exp. Immunol.*, 100:186-193, 1995.
Barrett et al., *Blood*, 95:3323-3327, 2000.
Barrett et al., *Bone Marrow Transplant.*, 21:543-551, 1998.
Behre et al., *Methods*, 17:231-237, 1999.
Benjamini et al., *Adv. Exp. Med. Biol.*, 303:71-77, 1991.
Bernhard et al., *Cancer Res.*, 55:1099-1104, 1995.
Blomer et al., *J. Virol.*, 71(9):6641-6649, 1997.
Bocchia et al., *Blood*, 85:2680-2684, 1995.
Bocchia et al., *Blood*, 87:3587-3592, 1996.
Boon et al., *Immunol Today*, 18:267-268, 1997.
Boon et al., *Important Adv. Oncol.*, 53-69, 1994.
Bories et al., Cell, 59:959, 1989.
Borregaard and Cowland, *Blood*, 89:3503-3521, 1997.
Borrello et al., *Blood*, 95:3011-3019, 2000.
Bourdette et al., J. Immunol., 152:2510-2519, 1994.
Boussiotis et al., J. Exp. Med., 184:365-376, 1996.
Boussiotis et al., Res. Immunol., 146:140-149, 1995.
Braunschweig et al., *Blood*, 96:3291, 2000.
Brouwer et al., *Clin. Exp. Immunol.*, 98:448-453, 1994.
Brutlag et al., *Comput. Appl. Biosci.*, 6(3):237-245, 1990.
Bukowski et al., *Clin. Cancer Res.*, 4(10):2337-47, 1998.
Burchert et al., *Blood*, 02:659, 2002.
Caldas et al., *Nat. Genet.*, 8(1):27-32, 1994.
Campanelli et al., *J. Exp. Med.*, 172:1709-1715, 1990.
Capaldi et al., *Biochem. Biophys. Res. Comm.*, 74(2):425-433, 1977.
Celis et al., *Proc. Natl. Acad. Sci. USA*, 91:2105-2109, 1994.
Chachu et al., *J. Virol.*, 82(13):6610-7, 2008.
Chen and Okayama, *Mol. Cell Biol.*, 7(8):2745-2752, 1987.
Chen et al., *Biochem. Biophys. Res. Commun.*, 200:1130-1135, 1994.
Chen et al., In: *Methods in Enzymology*, Academic Press, 211-219, 1996
Cheng et al., *Cancer Res.*, 54(21):5547-5551, 1994a.
Chou and Fasman, *Adv. Enzymol.*, 47:45-148, 1978b.
Chou and Fasman, *Annu. Rev. Biochem.*, 47:251-276, 1978a.
Chou and Fasman, *Biochemistry*, 13(2):211-222, 1974b.
Chou and Fasman, *Biophys. J.*, 26(3):385-399, 1979.
Christodoulides et al., *Microbiology*, 144(Pt 11):3027-37, 1998.
Clark et al., *Blood*, 98:2887-2893, 2001.
Cleary and Sklar, *Proc. Natl. Acad. Sci. USA*, (21):7439-7443, 1985.
Cleary et al., *J. Exp. Med.*, 164(1):315-320, 1986.
Collins, Jr. et al., *J. Clin. Oncol.*, 15:433-444, 1997.
Cortes et al., *Leukemia*, 12:455-462, 1998.
Cotten et al., *Proc. Natl. Acad. Sci. USA*, 89(13):6094-6098, 1992.
Coupar et al., *Gene*, 68:1-10, 1988.
Culver et al., *Science*, 256(5063):1550-1552, 1992.
Curiel, *Nat. Immun.*, 13(2-3):141-164, 1994.
Davidson et al., *J. Immunother.*, 21(5):389-98, 1998.
den Haan et al., *Science*, 268:1476-1480, 1995.
den Haan et al., *Science*, 279:1054-1057, 1998.

Dengler et al., *Br. J. Haematol.*, 89:250-257, 1995.
Dermime et al., *Blood*, 86, 1995.
Dermime et al., *Bone Marrow Transplant.*, 19:989-999, 1997.
Devergie et al., *Bone Marrow Transplant.*, 20:11-9, 1997.
Dickinson et al., *Nat. Med.*, 8:410-414, 2002.
Dillman, *Cancer Biother. Radiopharm.*, 14(1):5-10, 1999.
Dolstra et al., *J. Immunol.*, 158:560-565, 1997.
Drobyski et al., *Blood*, 83:1980-1987, 1994.
Dudley et al., *Science*, 298:850-854, 2002.
Dunbar et al., *Curr. Biol.*, 8:413-416, 1998.
Faber et al., *Biol. Blood Marrow Transplant.*, 2:31-36, 1996.
Faber et al., *Blood*, 86:2821-2828, 1995.
Faber et al., *J. Clin. Invest.*, 96:877-883, 1995.
Faderl et al., *Ann. Intern. Med.*, 131:207-219, 1999.
Fechheimer et al., *Proc. Natl. Acad. Sci. USA*, 84:8463-8467, 1987.
Fetrow and Bryant, *Biotechnology*, 11(4):479-484, 1993.
Fraley et al., *Proc. Natl. Acad. Sci. USA*, 76:3348-3352, 1979.
Franssen et al., *Kidney Int.*, 57:2195-1206, 2000.
Franssen et al., *Lancet.*, 347:116, 1996.
Friedmann, *Science*, 244:1275-1281, 1989.
Gale et al., *Ann. Intern. Med.*, 120:646-652, 1994.
Gallimore et al., *J. Exp. Med.*, 187:1383-1393, 1998.
Gao et al., *Blood*, 95:2198-2203, 2000.
Garlie et al., *J. Immunother.*, 22:336-345, 1999.
Gaschet et al., *J. Clin. Invest.*, 98:100-107, 1996.
Gaugler et al., *J. Exp. Med.*, 179:921-930, 1994.
Giralt and Kolb, *Curr. Opin. Oncol.*, 8:96-102, 1996.
Gopal, *Mol. Cell Biol.*, 5:1188-1190, 1985.
Goulmy et al., *N. Engl. J. Med.*, 334:281-285, 1996.
Graham and Van Der Eb, *Virology*, 52:456-467, 1973.
Grossman and Paul, *Proc. Natl. Acad. Sci. USA*, 89:10365-10369, 1992.
Grunhaus and Horwitz, *Seminar in Virology*, 3:237-252, 1992.
Hanibuchi et al., *Int. J. Cancer*, 78(4):480-485, 1998.
Harlan and Weintraub, *J. Cell Biol.*, 101:1094-1099, 1985.
Harlow and Lane, Antibodies: A Laboratory Manual. Cold Spring Harbor Laboratory Press, Cold Spring harbor, NY, 553-612, 1988.
Hellstrand et al., *Acta Oncol.*, 37(4):347-353, 1998.
Hensel et al., *Bone Marrow Transplant.*, 23:71-78, 1999.
Hermonat and Muzycska, *Proc. Natl. Acad. Sci. USA*, 81:6466-6470, 1984.
Herr et al., *J. Immunol. Methods*, 191:131-142, 1996.
Herr et al., *J. Immunol. Methods*, 203:141-152, 1997.
Horowitz et al., *Bone Marrow Transplant.*, 17(Suppl 3):S5-6, 1996.
Horwich et al. *J. Virol.*, 64:642-650, 1990.
Hui and Hashimoto, *Infect. Immun.*, 66(11):5329-36, 1998.
Husson et al., *J. Bacteriol.*, 172(2):519-524, 1990.
Hussussian et al., *Nat. Genet.*, 8(1):15-21, 1994.
Irie and Morton, *Proc. Natl. Acad. Sci. USA*, 83(22):8694-8698, 1986.
Irie et al., *Lancet*, 1(8641):786-787, 1989.
Jacobs et al., *Nature*, 327(6122):532-535, 1987.
Jameson and Wolf, *Comput. Appl. Biosci.*, 4(1):181-186, 1988.
Janetzki et al., *J. Immunol. Methods*, 234:1-12, 2000.
Jennette et al., *Semin. Diagn. Pathol.*, 18:3-13, 2001.
Johnson et al., In: *Biotechnology And Pharmacy*, Pezzuto et al. (Eds.), Chapman and Hall, NY, 1993.
Ju et al., *J. Neuropathol. Exp. Neurol.*, 59(3):241-50, 2000.
Kaeppler et al., *Plant Cell Reports*, 9:415-418, 1990.
Kamb et al., *Nat. Genet.*, 8(1):23-2, 1994.
Kamb et al., *Science*, 2674:436-440, 1994.
Kaneda et al., *Science*, 243:375-378, 1989.
Kato et al, *J. Biol. Chem.*, 266:3361-3364, 1991.
Katpally et al., *J. Virol.*, 82(5):2079-88, 2008.
Kelleher and Vos, *Biotechniques*, 17(6):1110-7, 1994.
Kerr et al., *Br. J. Cancer*, 26(4):239-257, 1972.
Klinman, *Curr. Prot. Immunol.*, 6.19:18, 1994.
Kochenderfer and Molldrem, *Curr. Oncol. Rep.* 3:193-200, 2001.
Kochenderfer et al., *Blood*, 100:3639-3645, 2002.
Kolb and Holler, *Curr. Opin. Oncol.*, 9:139-145, 1997.
Kolb et al., *Blood*, 86:2041-2050, 1995.
Kolb et al., *Bone Marrow Transplant*, 17:449-452, 1996.
Kwak et al., *Proc. Natl. Acad. Sci. USA*, 93:10972-10977, 1996.
Kyte and Doolittle, *J. Mol. Biol.*, 57(1):105-32, 1982.
Lalvani et al., *J. Exp. Med.*, 186:859-865, 1997.
Lam et al., *Nature.*, 354(6348):82-84, 1991.
Lam et al., *Chemical Rev.*, 97(2):411-448, 1997.
Laughlin et al., *J. Virol.*, 60(2):515-524, 1986.
Lebkowski et al., *Mol. Cell. Biol.*, 8(10):3988-3996, 1988.
Lee et al., *Nat. Med.*, 5:677-685, 1999.
Lehmann et al., *Eur. J. Immunol.*, 25:340-347, 1995.
Lemley et al., *Hybridoma*, 13(5):417-21, 1994.
Levine et al., *J. Hemather.*, 7:437-448, 1998.
Lewin et al., *Blood*, 100:2235-2242, 2002.
Lotte et al., *Adv. Tuberc. Res.*, 21:107-93; 194-245, 1984.
Lubbert et al., *Leukemia*, 13:1420-1427, 1999.
Luelmo, *Am. Rev. Respir. Dis.*, 125(3 Pt 2):70-72, 1982.
Mackinnon et al., *Bone Marrow Transplant.*, 15:591-594, 1995.
Maddaloni et al., *J. Immunol.*, 172(10):6221-8, 2004.
Maeurer et al., *J. Clin. Invest.*, 98:1633-1641, 1996.
Mann et al., *Cell*, 33:153-159, 1983.
Marchand et al., *Int. J. Cancer*, 63:883-885, 1995.
Marijt et al., *Blood* 82:3778-3785, 1995.
Marincola et al., *J. Immunother. Emphasis Tumor Immunol.*, 19:192-205, 1996.
Martin et al., *Nature*, 345(6277):739-743, 1990.
Matulonis et al., *Blood*, 85:2507-2515, 1995.
Mavroudis et al., *Bone Marrow Transplant.*, 17:793-799, 1996.
Mayet et al., *Eur. J. Clin. Invest.*, 27:893-899, 1997.
McLaughlin et al., *J. Virol.*, 62(6):1963-1973, 1988.
Miller et al., *Am. J. Clin. Oncol.*, 15(3):216-221, 1992.
Mitchell et al., *Ann. NY Acad. Sci.*, 690:153-166, 1993.
Mitchell et al., *J. Clin. Oncol.*, 8(5):856-869, 1990.
Molldrem et al., *Blood*, 88:2450-2457, 1996.
Molldrem et al., *Blood*, 90:1858, 1998.
Molldrem et al., *Blood*, 90:2529-2534, 1997.
Molldrem et al., *Br. J. Haematol.*, 102:1314-1322, 1998.
Molldrem et al., *Cancer Res.*, 59:2675-2681, 1999.
Molldrem et al., *Curr. Opin. Hematol.*, 9:503-508, 2002.
Molldrem et al., *J. Clin. Invest.*, 111:639-647, 2003.
Molldrem et al., *Nat. Med.*, 6:1018-1023, 2000.
Molldrem et al., *Oncogene*, 21:8668-8673, 2002.
Moola et al., *Cell*, 144(1):132-142, 2011.
Morgan et al., *J. Immunol.*, 160:643-651, 1998.
Mori et al., *Cancer Res.*, 54(13):3396-3397, 1994.
Morton et al., *Arch. Surg.*, 127:392-399, 1992.
Muller-Berat et al., *Clin. Immunol. Immunopathol.*, 70:51-59, 1994.
Muzyczka, *Curr. Topics Microbiol. Immunol.*, 158:97-129, 1992.
Nakamoto et al., *J. Immunol.*, 158:5692-5697, 1997.
Naldini et al., *Science*, 272(5259):263-267, 1996.
Nanda and Sercarz, *Cell*, 82:13-17, 1995.

Neal et al., *Infection Immunity*, 78(1):552-61, 2010.
Nelson et al., *Blood*, 88:580-589, 1996.
Nestle et al., *Nature Med.*, 4:328-332, 1998.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Nobri et al., *Nature* (London), 368:753-756, 1995.
Okamoto et al., *Proc. Natl. Acad. Sci. USA*, 1(23):11045-11049, 1994.
Omirulleh et al., *Plant Mol. Biol.*, 21(3):415-28, 1993.
Orlow et al., *Cancer Res*, 54(11):2848-2851, 1994.
Papadopoulos et al., *Blood*, 90:4938-4946, 1997.
Pardoll, *Current Opin. Immunol.*, 14:619-623, 1992.
Pardoll, *Nature Rev. Immunol.*, 2:227-238, 2002.
Pardoll, *Nature*, 369:357, 1994.
Parker et al., *J. Immunol.*, 152:163, 1994.
Parkhurst et al., *J. Immunol.*, 157:2539-2548, 1996.
Paskind et al., *Virology*, 67:242-248, 1975.
PCT Appln, WO 91/16347
PCT Appln. WO 94/09699
PCT Appln. WO 95/06128
Pietras et al., *Oncogene*, 17(17):2235-49, 1998.
Pinilla-Ibarz et al., *Blood*, 95:1781-1787, 2000.
Pinna et al., *Eur. J. Immunol.*, 39(5):1260-1270, 2009.
Porter-Jordan & Lippman, *Breast Cancer*, 8:73-100, 1994.
Potrykus et al., *Mol. Gen. Genet.*, 199:183-188, 1985.
Qin et al., *Proc. Natl. Acad. Sci. USA*, 95(24):14411-14416, 1998.
Rabinovich et al., *Science*, 265(5177):1401-1404, 1994.
Rammensee et al., *Immunogenetics*, 41:178-228, 1995.
Ravindranath and Morton, *Intern. Rev. Immunol.*, 7: 303-329, 1991.
Rees et ah, *Proc. Natl. Acad. Sci. USA*, 96:9781-9786, 1999.
Reich-Zeliger et al., *Immunity*, 13:507-515, 2000.
Remington's Pharmaceutical Sciences, 15th ed., pages 1035-1038 and 1570-1580, Mack Publishing Company, Easton, Pa., 1980.
Restifo et al., *J. Exp. Med.*, 177:265-272, 1993.
Riddell and Greenberg, *Annu. Rev. Immunol.*, 13:545-586, 1995.
Riddell and Greenberg, *Cancer Treat Res.*, 76:337-369, 1995.
Riddell and Greenberg, *Curr. Top Microbiol. Immunol.*, 189:9-34, 1994.
Riddell et al., *Science*, 257:238-241, 1992.
Ridgeway, In: *Vectors: A survey of molecular cloning vectors and their uses*, Rodriguez and Denhardt (Eds.), Stoneham:Butterworth, 467-492, 1988.
Rippe et al., *Mol. Cell Biol.*, 10:689-695, 1990.
Rosenberg and White, *J. Immunother. Emphasis. Tumor Immunol.*, 19:81-84, 1996.
Rosenberg et al., *Ann. Surg.* 210(4):474-548, 1989.
Rosenberg et al., *Nature Med.*, 4:321-327, 1998.
Rosenberg et al., *N Engl. J. Med.*, 319:1676, 1988.
Salter and Cresswell, *Embo. J.*, 5:943-949, 1986.
Santini et al., *J. Exp. Med.*, 191:1777-1788, 2000.
Savage et al., *Immunity*, 10:485-492, 1999.
Savige et al., *Am. J. Clin. Pathol.*, 111:507-513, 1999.
Scheibenbogen et al., *Blood*, 100:2132-2137, 2002.
Scheibenbogen et al., *Int. J. Cancer*, 71:932-936, 1997.
Serrano et al., *Nature*, 366:704-707, 1993.
Serrano et al., *Science*, 267(5195):249-252, 1995.
Sette et al., *J. Immunol.*, 153:5586-5592, 1994.
Shlomchik et al., *Science*, 285:412-415, 1999.
Sibelius et al., *J. Exp. Med.*, 187:497-503, 1998.
Snapper et al., *Proc. Natl. Acad. Sci. USA*, 85(18):6987-6991, 1988.
Stark, G. R., Kerr, I. M., Williams, B. R., Silverman, R. H. & Schreiber, R. D. How cells respond to interferons. *Annu Rev Biochem* 67, 227-64 (1998).
Sturrock et al., *J. Biol. Chem.*, 267:21193, 1992.
Takada et al., *J. Clin. Microbiol.*, 33(3):658-660, 1995.
Tanaka et al., *Cancer Res.*, 57:4465-4468, 1997.
Tanaka et al., *Genes Cells*, 3:29-37, 1998.
Temin, In: *Gene Transfer*, Kucherlapati (Ed.), NY, Plenum Press, 149-188, 1986.
Teshima et al., *Nat. Med.*, 8:575-581, 2002.
Toes et al., *Int. J. Cancer*, 66:686-691, 1996.
Toes et al., *J. Immunol.*, 156:3911-3918, 1996.
Toes et al., *Proc. Natl. Acad. Sci. USA*, 93:7855-7860, 1996.
Tratschin et al., *Mol. Cell. Biol.*, 4:2072-2081, 1984.
Tsujimoto and Croce, *Proc. Natl. Acad. Sci. USA*, 83(14):5214-5218, 1986.
Tsujimoto et al., *Science*, 228(4706):1440-1443, 1985.
Tsukada et al., *J. Exp. Clin. Cancer Res.*, 16:171-176, 1997.
van der Bruggen et al., *Eur. J. Immunol.*, 124:3038-3043, 1994.
van der Harst et al., *Blood*, 83:1060-1066, 1994.
van Lochem et al., *Bone Marrow Transplant.*, 10:181-183, 1992.
van Rhee et al., *Blood*, 83, 1994.
Verdijk et al., *J. Immunol.*, 163:57-61, 1999.
Wada et al., *Nucleic Acids Res.* 18:2367-2411, 1990.
Walker et al., Science, 326(5950):285-289, 2009.
Wang et al., *Biol. Blood Marrow Transplant.*, 6:118, 2000.
Weinberger et al., *Science*, 228:740-742, 1985.
Williams et al., *J. Immunol.*, 152:4722-4732, 1994.
Wobus et al., *PLoS Biology*, 2(12):e432, 2004.
Wolf et al., *Comput. Appl. Biosci.*, 4(1):187-191, 1988.
Wong et al., *Gene*, 10:87-94, 1980.
Yamamoto et al., *Jpn. J. Cancer Res.*, 79:866-873, 1988.
Yee et al., *J. Immunol.*, 162:2227-2234, 1999.
Yu et al., *Nat. Biotechnol.*, 23746-751, 2005.
Yin et al., *J. Biol. Resp. Modif.*, 8:190-205, 1989.
Zarour et al., *J. Invest. Dermatol.*, 107:63-67, 1996.
Zeh et al., *J. Immunol.*, 162:989-994, 1999.
Zufferey et al., *Nat. Biotechnol.*, 15(9):871-875, 1997.

What is claimed is:

1. A method of selecting a peptoid mimetic of a protective B cell epitope comprising:
   (a) providing a monoclonal selecting antibody that can inhibit or attenuate a disease, or neutralize a toxin;
   (b) providing a peptoid library;
   (c) eliminating from said peptoid library those peptoids that bind outside the antigen combining region of the selecting antibody, thereby creating a depleted library;
   (d) adding said selecting antibody to the depleted library;
   (e) selecting antibody-bound peptoid from peptoids not bound by said selecting antibody using a ligand for said monoclonal antibody; wherein said selecting comprises:
      (i) using protein A/G-decorated beads to select antibody-bound peptoids;
      (ii) subjecting protein A/G-bound antibody-peptoid complexes to conditions that release protein A from said antibody, and further release said selecting antibody from said peptoid; and
      (iii) isolating said peptoid from said protein A/G decorated AG-coated beads and from said selecting antibody, or, (i) using anti-antibody to select antibody-bound peptoids;

(ii) subjecting anti-antibody-bound antibody-peptoid complexes to conditions that release anti-antibody from said antibody, and further release said selecting antibody from said peptoid; and (iii) isolating said peptoid from said anti-antibody and from said selecting antibody;

(f) validating the selected peptoids from step (e) by stripping the bound reagents, adding fresh selecting antibody and an enzyme-linked to a ligand that will change color when a substrate for that enzyme is added, wherein a peptoid that binds to said selecting antibody in step (f) is a peptoid mimetic of a protective B cell epitope bound by the selecting antibody; and (g) combining a peptoid selected in step (f) to a carrier molecule that renders the selected peptoid immunogenic.

2. The method of claim 1, wherein said selecting antibody binds to a chemical, drug, allergen, toxin, virus, bacterium, fungus, prion, or parasite.

3. The method of claim 1, further comprising obtaining the sequence of a peptoid selected in step (f).

4. The method of claim 3, wherein obtaining comprises referencing a code or pattern that correlates to a predetermined sequence.

5. The method of claim 3, wherein obtaining comprises Edman degradation, mass spectrometry, circular dichroism, nuclear magnetic resonance, or X-ray crystallography.

6. The method of claim 1, further comprising immunizing a vertebrate with said peptoid-carrier complex.

7. The method of claim 6, wherein said carrier molecule is any non-self protein lacking T and B cell epitopes that cross react with self T and B cell epitopes.

8. The method of claim 6, wherein the peptoid is displayed on said carrier at up to $10^7$ copies per carrier molecule.

9. The method of claim 6, further comprising the addition and co-administration of an adjuvant or other immunostimulatory agent.

10. The method of claim 9, wherein said immunostimulatory agent is a cytokine, a ligand for a Toll-like receptor (TLR), or liposome with said peptoid-carrier complex.

11. The method of claim 6, further comprising obtaining post-immunization serum from said vertebrate.

12. The method of claim 11, further comprising determining the binding of post-immunization serum to a disease-causing agent or component thereof to which said selecting antibody binds.

13. The method of claim 12, wherein said binding is determined in a competitive format with said selecting antibody.

14. The method of claim 11, further comprising determining the ability of said post-immunization serum to inhibit or attenuate disease.

15. The method of claim 14, wherein inhibit or attenuate comprises complement-dependent neutralization, complement-independent neutralization, direct inhibition of growth, antibody dependent cell mediated cytotoxicity (ADCC), opsonization, inhibition of binding to a target cell, inhibition of infection or toxicity, elimination by the reticuloendothelial system (RES), or prevention of homing to a site where disease will manifest.

16. The method of claim 1, wherein said carrier molecule is any non-self protein lacking T and B cell epitopes that cross react with self T and B cell epitopes.

17. The method of claim 1, wherein said carrier molecule is a liposome or nanoparticle.

18. The method of claim 1, further comprising assessing the binding of said selecting antibody with said peptoid-carrier complex.

19. The method of claim 1, wherein said peptoid library is displayed on a solid support.

20. The method of claim 19, wherein said solid support is a glass slide, a chip or a population of beads.

21. The method of claim 1, wherein said protein AG-coated beads are magnetic beads.

22. The method of claim 1 wherein said anti-antibody is linked to a surface or a ligand.

* * * * *

UNITED STATES PATENT AND TRADEMARK OFFICE
CERTIFICATE OF CORRECTION

PATENT NO. : 9,770,504 B2
APPLICATION NO. : 14/888297
DATED : September 26, 2017
INVENTOR(S) : Ellen S. Vitetta Page 1 of 1

It is certified that error appears in the above-identified patent and that said Letters Patent is hereby corrected as shown below:

In the Specification

In Column 1, Lines 14-18, delete paragraph and insert:
--This invention was made with government support under grant number CA148271 awarded by The National Institutes of Health. The government has certain rights in the invention.-- therefor.

Signed and Sealed this
Fourth Day of August, 2020

Andrei Iancu
*Director of the United States Patent and Trademark Office*